United States Patent [19]

Babu et al.

[11] Patent Number: 5,925,759

[45] Date of Patent: Jul. 20, 1999

[54] METHODS OF MAKING HIV-PROTEASE INHIBITORS AND INTERMEDIATES FOR MAKING HIV-PROTEASE INHIBITORS

[75] Inventors: Srinivasan Babu; Bennett C. Borer, both of San Diego; Travis P. Remarchuk, Irvine; Robert J. Szendroi; Kathleen R. Whitten, both of San Diego; Juliette K. Busse, Solana Beach; Kim F. Albizati, San Diego, all of Calif.

[73] Assignee: Agouron Pharmaceuticals, Inc., La Jolla, Calif.

[21] Appl. No.: 08/923,947

[22] Filed: Sep. 5, 1997

Related U.S. Application Data

[60] Provisional application No. 60/025,515, Sep. 5, 1996.

[51] Int. Cl.⁶ ...................... C07D 215/58; C07D 263/04; C07D 317/04; C07D 413/04

[52] U.S. Cl. .......................... 546/164; 548/224; 548/239; 548/469; 548/478; 549/33; 549/454; 558/59; 562/582

[58] Field of Search ...................................... 548/239, 478

[56] References Cited

U.S. PATENT DOCUMENTS 5,705,647 1/1998 Babu et al. .

*Primary Examiner*—Johann Richter
*Assistant Examiner*—Taofiq A. Solola
*Attorney, Agent, or Firm*—Finnegan, Henderson, Farabow, Garrett & Dunner, L.L.P.

[57] ABSTRACT

HIV protease inhibitors inhibit or block the biological activity of the HIV protease enzyme, causing the replication of the HIV virus to terminate. These compounds can be prepared by the novel methods of the present invention using the novel inventive intermediates.

12 Claims, No Drawings

METHODS OF MAKING HIV-PROTEASE INHIBITORS AND INTERMEDIATES FOR MAKING HIV-PROTEASE INHIBITORS

RELATED APPLICATION DATA

This application claims priority benefits under 35 U.S.C. § 119 based on U.S. Provisional patent appln. Ser. No. 60/025,515, filed Sep. 5, 1996. This provisional application is entirely incorporated herein by reference. Additionally, this application relates to the following U.S. patent applications:

| U.S. Patent Appln. No. | Filing Date |
| --- | --- |
| 08/133,543 | October 7, 1993 |
| 08/133,696 | October 7, 1993 |
| 08/190,764 | February 2, 1994 |
| 08/481,833 | June 7, 1995 |
| 08/708,607 | September 5, 1996 |

Each of these U.S. patent applications also is entirely incorporated herein by reference.

INTRODUCTION

Treatment of HIV-infected individuals is one of the most pressing biomedical problems of recent times. A promising new therapy has emerged as an important method for preventing or inhibiting the rapid proliferation of the virus in human tissue. HIV-protease inhibitors block a key enzymatic pathway in the virus resulting in substantially decreased viral loads, which slows the steady decay of the immune system and its resulting deleterious effects on human health. The HIV-protease inhibitor nelfinavir mesylate

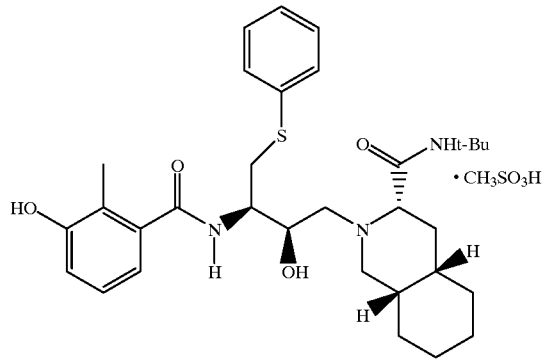

has been shown to be an effective treatment for HIV-infected individuals. Nelfinavir mesylate is disclosed in U.S. Pat. No. 5,484,926, issued Jan. 16, 1996. This patent is entirely incorporated by reference into this patent application. Methods for preparing nelfinavir mesylate from nelfinavir free base are disclosed in U.S. Pat. No. 5,484,926, as well as U.S. patent appln. Ser. No. 08/708,411 of inventors M. Deason and K. Whitten, entitled "Intermediates for Making HIV-Protease Inhibitors and Methods of Making HIV-Protease Inhibitors", filed on Sep. 5, 1996, which application is entirely incorporated herein by reference.

SUMMARY OF THE INVENTION

The present invention relates to the novel compounds illustrated below. These compounds are useful as intermediates and starting materials for the preparation of nelfinavir free base and nelfinavir mesylate.

A first compound according to this invention is a compound of formula 6, as follows:

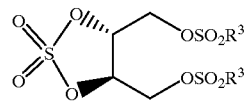

6 wherein each $R^3$ is independently an aryl group or an alkyl group; or a pharmaceutically acceptable salt or solvate thereof.

A second compound according to this invention is a compound of formula 6a:

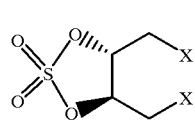

6a wherein each X is independently a halogen; or a pharmaceutically acceptable salt or solvate thereof.

A third compound according to this invention is a compound of formula 7:

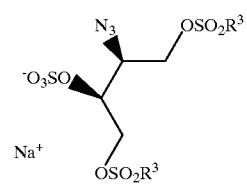

7 wherein each $R^3$ is independently an aryl group or an alkyl group; or a pharmaceutically acceptable salt or solvate thereof.

A fourth compound according to this invention is a compound of formula 8:

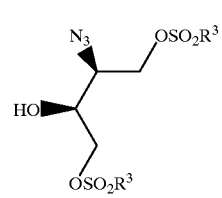

8 wherein each $R^3$ is independently an aryl group or an alkyl group; or a pharmaceutically acceptable salt or solvate thereof.

A fifth compound according to the invention is a compound of formula 9:

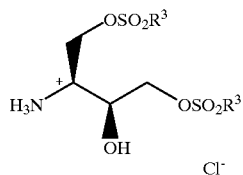

wherein each R³ is independently an aryl group or an alkyl group; or a pharmaceutically acceptable salt or solvate thereof.

A sixth compound according to this invention is a compound of formula 10:

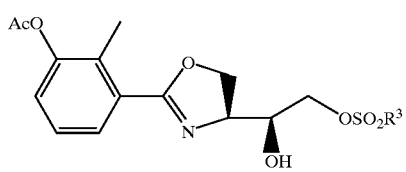

wherein R³ is an aryl group or an alkyl group; or a pharmaceutically acceptable salt or solvate thereof.

A seventh compound according to this invention is a compound of formula 7a:

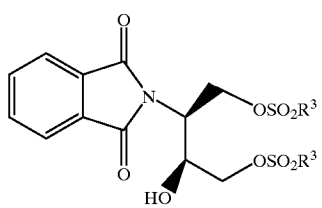

wherein each R³ is independently an aryl group or an alkyl group; or a pharmaceutically acceptable salt or solvate thereof.

An eighth compound according to this invention is a compound of formula 8a:

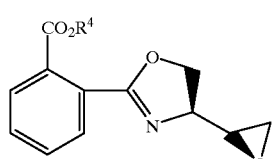

wherein R⁴ is an alkyl group; or a pharmaceutically acceptable salt or solvate thereof.

A ninth compound according to this invention is a compound of formula 9a:

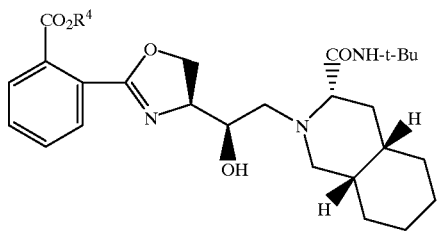

wherein R⁴ is an alkyl group; or a pharmaceutically acceptable salt or solvate thereof.

A tenth compound according to this invention is a compound of formula 10a:

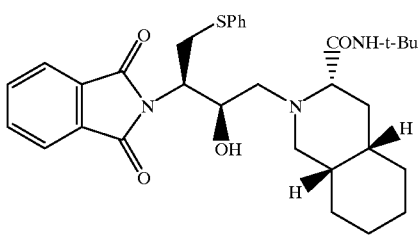

or a pharmaceutically acceptable salt or solvate thereof.

This invention further relates to processes for making and using the compounds and intermediates described above. For example, these compounds can be used to prepare nelfinavir free base and nelfinavir mesylate.

A first method according to the invention relates to a method of making a compound of formula 6:

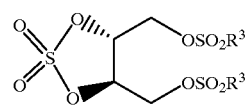

wherein each R³ is independently an aryl group or an alkyl group, by converting, under sufficient conditions, a compound of formula 5:

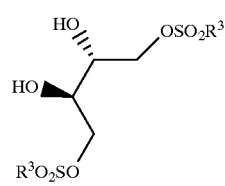

wherein each R³ is independently an aryl group or an alkyl group, to the compound of formula 6 shown above.

In a second method according to this invention, a compound of formula 6a is produced:

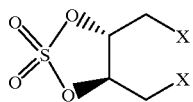

6a wherein each X is independently a halogen. In this method, the compound according to formula 5 (illustrated above) is converted, under sufficient conditions, to the compound of formula 6a.

This invention further relates to methods of making a compound of formula 7:

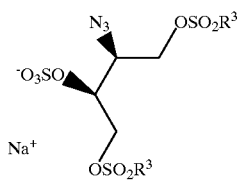

7 wherein each $R^3$ is independently an aryl group or an alkyl group. In one method, a compound of formula 6:

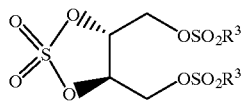

6 wherein each $R^3$ is independently an aryl group or an alkyl group, is converted, under sufficient conditions, to the compound of formula 7. In another method, a compound according to formula 6a:

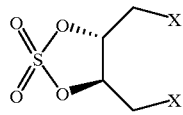

6a wherein each X is independently a halogen, is converted, under sufficient conditions, to the compound of formula 7.

Another method according to this invention relates to a method of making a compound of formula 8:

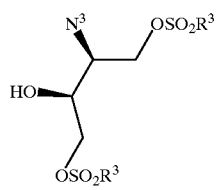

8 wherein each $R^3$ is independently an aryl group or an alkyl group. The compound according to formula 8 is produced by converting, under sufficient conditions, a compound of formula 7:

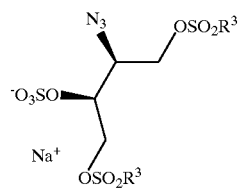

7 wherein each $R^3$ is independently an aryl group or an alkyl group, to the compound of formula 8.

In another method according to this invention, a compound according to formula 8 (illustrated above), can be converted, under sufficient conditions, to a compound of formula 9:

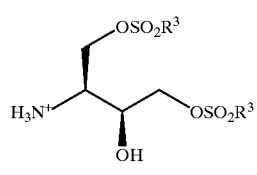

9 wherein each $R^3$ is independently an aryl group or an alkyl group.

Yet another method according to this invention relates to a method of making a compound of formula 10:

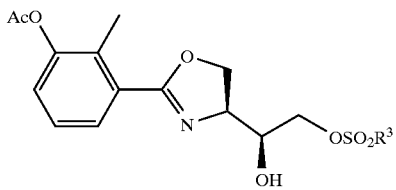

10 wherein $R^3$ is an aryl group or an alkyl group. In this method, a compound of formula 9:

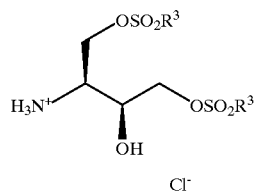

9 wherein each $R^3$ is independently an aryl group or an alkyl group, is converted, under sufficient conditions, to a compound of formula 10.

This invention also relates to a method of making a compound of formula 11:

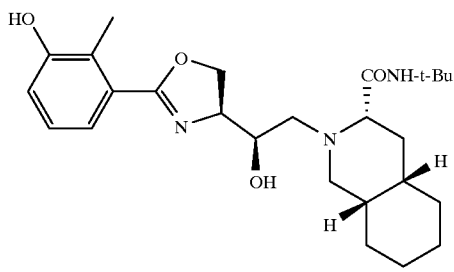

11 by converting, under sufficient conditions, a compound of formula 10:

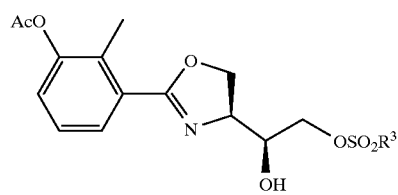

10 wherein R³ is an aryl group or an alkyl group, to a compound of formula 11.

As mentioned above, another compound or intermediate according to this invention is a compound of formula 7a:

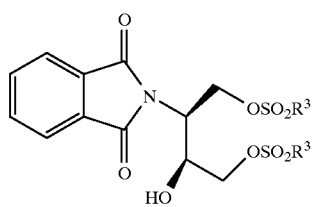

7a wherein each R³ is independently an aryl group or an alkyl group. This material can be made, in accordance with another method of this invention, by converting, under sufficient conditions, a compound of formula 6:

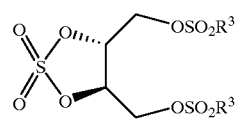

6 wherein each R³ is independently an aryl group or an alkyl group, to the compound of formula 7a. In an alternative method according to this invention, the compound according to formula 7a (shown above) can be produced by converting, under sufficient conditions, a compound of formula 6a:

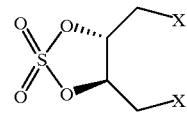

6a wherein each X is independently a halogen, to the compound of formula 7a.

Another method according to this invention relates to a method of making a compound of formula 8a:

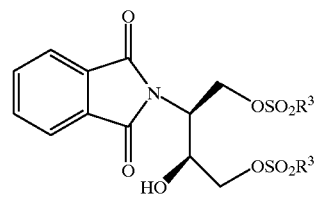

8a wherein R⁴ is an alkyl group. This compound is produced by converting, under sufficient conditions, a compound of formula 7a:

7a wherein each R³ is independently an aryl group or an alkyl group, to the compound of formula 8a.

In another method according to the invention, a compound of formula 9a:

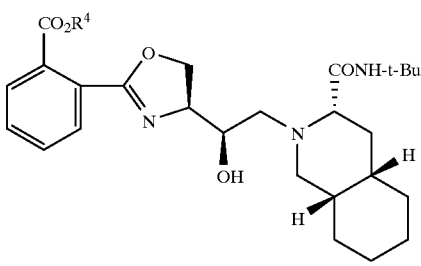

9a wherein R⁴ is an alkyl group, can be produced by converting, under sufficient conditions, a compound of formula 8a:

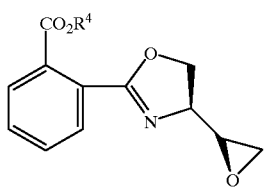

8a wherein R⁴ is an alkyl group, to the compound of formula 9a.

Yet another method according to this invention relates to a method of making a compound of formula 10a:

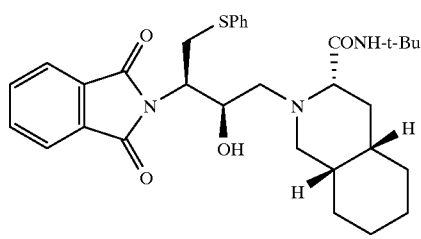

10a by converting, under sufficient conditions, a compound of formula 9a:

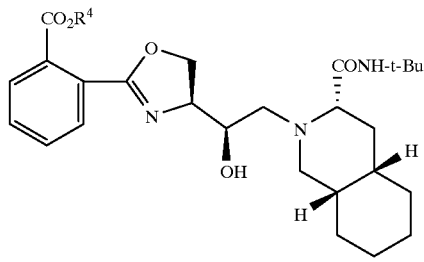

9a wherein R⁴ is an alkyl group, to the compound of formula 10a.

The compound according to formula 10a (shown above) can be used in another method of this invention to produce a compound of formula 11a:

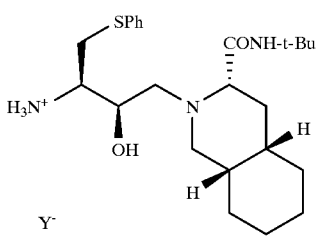

11a wherein Y⁻ is a suitable salt anion. In this method, the compound of formula 10a is converted, under sufficient conditions, to the compound of formula 11a.

The compounds and intermediates according to the invention advantageously can be used to produce nelfinavir mesylate:

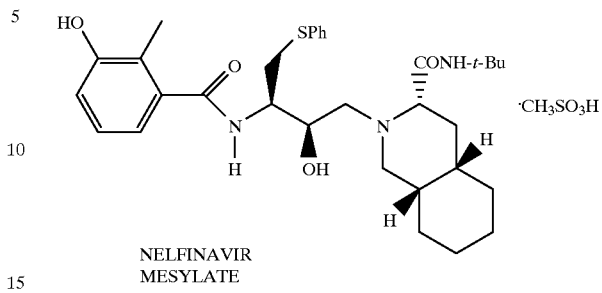

NELFINAVIR MESYLATE

In one method, a compound of formula 10:

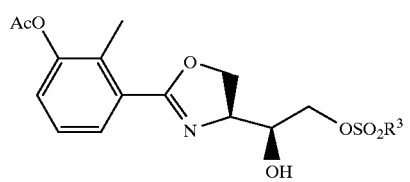

10 wherein R³ is an aryl group or an alkyl group, is converted, under sufficient conditions, to a compound of formula 11:

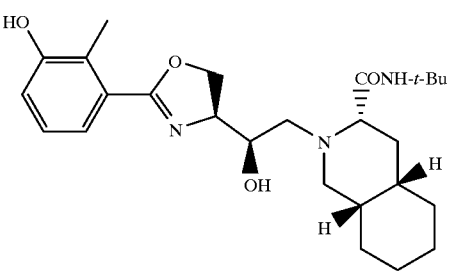

11

The compound according to formula 11 then is converted, under sufficient conditions, to a compound of formula 12:

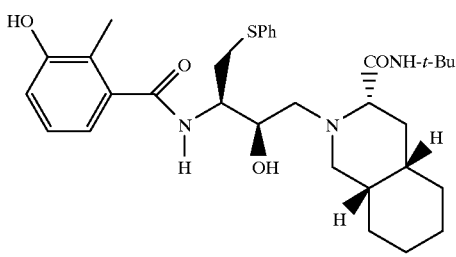

12

The compound according to formula 12 is then converted to nelfinavir mesylate.

A second method according to the invention for making nelfinavir mesylate (illustrated above) includes converting, under sufficient conditions, a compound of formula 10a:

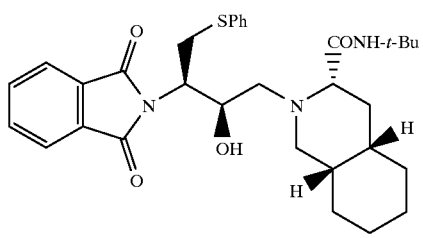

10a to a compound of formula 11a:

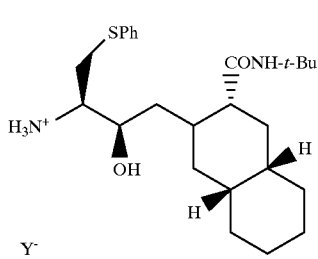

11a wherein $Y^-$ is a suitable salt anion. The compound of formula 11a then is converted, under sufficient conditions, to a compound of formula 12 (shown above), which then is converted, under sufficient conditions, to nelfinavir mesylate.

DESCRIPTION OF THE INVENTION

The present inventors have discovered useful novel intermediate compounds that can be used in several novel reaction schemes to make nelfinavir mesylate. More specifically, the present invention relates to new processes that have been developed to prepare nelfinavir free base, the penultimate intermediate of the raw drug nelfinavir mesylate (Schemes 1, 2 and 3). In addition to being operationally simple, these processes utilize cheap, commercially available raw materials and offer an alternative to the more expensive chloro-alcohol based chemistry that has been used for manufacture (see HIV Protease Inhibitors, Intl. Patent No. WO 95/09843). These new processes proceed through cyclic sulfates of general structure 6 or 6a:

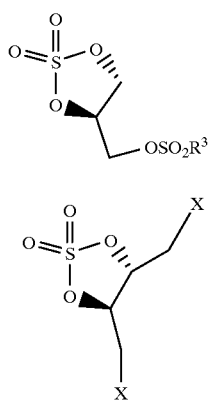

6

6a where $R^3$ is aryl or alkyl and X is a leaving group. These cyclic sulfates are novel 4-carbon electrophilic species derived from (2S,3S)-(−)tartaric acid, a substance commercially available from many suppliers. Such intermediates are new chemical entities that possess leaving group ability at 4 contiguous carbons. Such ambident electrophilicity can be selectively unmasked in the production of 4 carbon units useful in nelfinavir free base synthesis. These intermediates are general synthons for the production of 4-carbon units bearing 4 carbon-heteroatom bonds, two of which are at stereogenic centers.

Using the intermediates and compounds described in this application, as well as the methods described herein, one can prepare nelfinavir free base and nelfinavir mesylate, compounds useful as HIV-protease inhibitors. The following detailed description describes various specific examples and reaction schemes that can be used in accordance with this invention. These examples and reaction schemes should be considered as illustrating the invention and not as limiting the same.

Furthermore, in this application, Applicants describe certain theories and reaction mechanisms in an effort to explain how and why this invention works in the manner in which it works. These theories and mechanisms are set forth for informational purposes only. Applicants are not to be bound by any particular chemical, physical, or mechanical theory of operation.

Definitions

As used in the present application, the following definitions apply:

The term "alkyl" as used herein refers to substituted or unsubstituted, straight or branched chain groups, preferably, having one to eight, more preferably having one to six, and most preferably having from one to four carbon atoms. The term "$C_1$–$C_6$ alkyl" represents a straight or branched alkyl chain having from one to six carbon atoms. Exemplary $C_1$–$C_5$ alkyl groups include methyl, ethyl, n-propyl, isopropyl, butyl, isobutyl, sec-butyl, t-butyl, pentyl, neopentyl, hexyl, isohexyl, and the like. The term "$C_1$–$C_6$ alkyl" includes within its definition the term "$C_1$–$C_4$ alkyl".

The term "cycloalkyl" represents a substituted or unsubstituted, saturated or partially saturated, mono- or poly-carbocyclic ring, preferably having 5–14 ring carbon atoms. Exemplary cycloalkyls include monocyclic rings having from 3–7, preferably 3–6, carbon atoms, such as cyclopropyl, cyclobutyl, cyclopentyl, cyclohexyl, cycloheptyl and the like. An exemplary cycloalkyl is a $C_5$–$C_7$ cycloalkyl, which is a saturated hydrocarbon ring structure containing from five to seven carbon atoms.

The term "aryl" as used herein refers to an aromatic, monovalent monocyclic, bicyclic, or tricyclic radical containing 6, 10, 14, or 18 carbon ring atoms, which may be unsubstituted or substituted, and to which may be fused one or more cycloalkyl groups, heterocycloalkyl groups, or heteroaryl groups, which themselves may be unsubstituted or substituted by one or more suitable substituents. Illustrative examples of aryl groups include, but are not limited to, phenyl, naphthyl, anthryl, phenanthryl, fluoren-2-yl, indan-5-yl, and the like.

The term "halogen" represents chlorine, fluorine, bromine or iodine. The term "halo" represents chloro, fluoro, bromo or iodo.

The term "carbocycle" represents a substituted or unsubstituted aromatic or a saturated or a partially saturated 5–14 membered monocyclic or polycyclic ring, such as a 5- to 7-membered monocyclic or 7- to 10-membered bicyclic ring, wherein all the ring members are carbon atoms.

A "heterocycloalkyl group" is intended to mean a non-aromatic, monovalent monocyclic, bicyclic, or tricyclic radical, which is saturated or unsaturated, containing 3, 4, 5, 6, 7, 8, 9, 10, 11, 12, 13, 14, 15, 16, 17, or 18 ring atoms, and which includes 1, 2, 3, 4, or 5 heteroatoms selected from nitrogen, oxygen and sulfur, wherein the radical is unsubstituted or substituted, and to which may be fused one or more cycloalkyl groups, aryl groups, or heteroaryl groups, which themselves may be unsubstituted or substituted. Illustrative examples of heterocycloalkyl groups include, but are not limited to, azetidinyl, pyrrolidyl, piperidyl, piperazinyl, morpholinyl, tetrahydro-2H-1,4-thiazinyl, tetrahydrofuryl, dihydrofuryl, tetrahydropyranyl, dihydropyranyl, 1,3-dioxolanyl, 1,3-dioxanyl, 1,4-dioxanyl, 1,3-oxathiolanyl, 1,3-oxathianyl, 1,3-dithianyl, azabicylo[3.2.1]octyl, azabicylo[3.3.1]nonyl, azabicylo[4.3.0]nonyl, oxabicylo[2.2.1]heptyl, 1,5,9-triazacyclododecyl, and the like.

A "heteroaryl group" is intended to mean an aromatic monovalent monocyclic, bicyclic, or tricyclic radical containing 5, 6, 7, 8, 9, 10, 11, 12, 13, 14, 15, 16, 17, or 18 ring atoms, including 1, 2, 3, 4, or 5 heteroatoms selected from nitrogen, oxygen and sulfur, which may be unsubstituted or substituted, and to which may be fused one or more cycloalkyl groups, heterocycloalkyl groups, or aryl groups, which themselves may be unsubstituted or substituted. Illustrative examples of heteroaryl groups include, but are not limited to, thienyl, pyrrolyl, imidazolyl, pyrazolyl, furyl, isothiazolyl, furazanyl, isoxazolyl, thiazolyl, pyridyl, pyrazinyl, pyrimidinyl, pyridazinyl, triazinyl, benzo[b]thienyl, naphtho[2,3-b]thianthrenyl, isobenzofuranyl, chromenyl, xanthenyl, phenoxathienyl, indolizinyl, isoindolyl, indolyl, indazolyl, purinyl, isoquinolyl, quinolyl, phthalazinyl, naphthyridinyl, quinoxyalinyl, quinzolinyl, benzothiazolyl, benzimidazolyl, tetrahydroquinolinyl, cinnolinyl, pteridinyl, carbazolyl, beta-carbolinyl, phenanthridinyl, acridinyl, perimidinyl, phenanthrolinyl, phenazinyl, isothiazolyl, phenothiazinyl, and phenoxazinyl.

Suitable protecting groups are recognizable to those skilled in the art. Examples of suitable protecting groups can be found in T. Green & P. Wuts, *Protective Groups in Organic Synthesis* (2d ed. 1991), which is incorporated herein by reference.

Suitable salt anions include, but are not limited to, inorganics such as halogens, pseudohalogens, sulfates, hydrogen sulfates, nitrates, hydroxides, phosphates, hydrogen phosphates, dihydrogen phosphates, perchloroates, and related complex inorganic anions; and organics such as carboxylates, sulfonates, bicarbonates and carbonates.

The term "DABCO" as used herein refers to the reagent 1,4-diazabicyclo[2.2.2]octane.

The term "DBN" as used herein refers to the reagent 1,5-diazabicyclo[4.3.0]non-5-ene.

The term "DBU" as used herein refers to the reagent 1,8-diazabicyclo[5.4.0]undec-7-ene.

The term "MTBE" as used herein refers to the solvent methyl t-butyl ether.

The term "arylsufonic acid" as used herein refers to substituted or unsubstituted groups of formula:

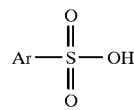

wherein Ar is an aromatic ring.

The term "leaving group" as used herein refers to any group that departs from a molecule in a substitution reaction by breakage of a bond. Examples of leaving groups include, but are not limited to, halides, arenesulfonates, alkylsulfonates, and triflates.

The term "DMF" as used herein refers to the solvent N,N-dimethylformamide.

The term "THF" as used herein refers to the solvent tetrahydrofuran.

The term "DMAC" as used herein refers to the solvent N,N-dimethylacetamide.

Examples of substituents for alkyl and aryl include mercapto, thioether, nitro ($NO_2$), amino, aryloxyl, halogen, hydroxyl, alkoxyl, and acyl, as well as aryl, cycloalkyl and saturated and partially saturated heterocycles. Examples of substituents for cycloalkyl include those listed above for alkyl and aryl, as well as aryl and alkyl.

Exemplary substituted aryls include a phenyl or naphthyl ring substituted with one or more substituents, preferably one to three substituents, independently selected from halo, hydroxy, morpholino($C_1$–$C_4$)alkoxy carbonyl, pyridyl ($C_1$–$C_4$)alkoxycarbonyl, halo ($C_1$–$C_4$)alkyl, $C_1$–$C_4$ alkyl, $C_1$–$C_4$alkoxy, carboxy, $C_1$–$C_4$ alkoxycarbonyl, carbamoyl, N—($C_1$–$C_4$)alkylcarbamoyl, amino, $C_1$–$C_4$alkylamino, di($C_1$–$C_4$)alkylamino or a group of the formula —$(CH_2)_a$-$R^7$ where a is 1, 2, 3 or 4; and $R^7$ is hydroxy, $C_1$–$C_4$ alkoxy, carboxy, $C_1$–$C_4$ alkoxycarbonyl, amino, carbamoyl, $C_1$–$C_4$ alkylamino or di($C_1$–$C_4$)alkylamino.

Another substituted alkyl is halo($C_1$–$C_4$)alkyl, which represents a straight or branched alkyl chain having from one to four carbon atoms with 1–3 halogen atoms attached to it. Exemplary halo($C_1$–$C_4$)alkyl groups include chloromethyl, 2-bromoethyl, 1-chloroisopropyl, 3-fluoropropyl, 2,3-dibromobutyl, 3-chloroisobutyl, iodo-t-butyl, trifluoromethyl and the like.

Another substituted alkyl is hydroxy($C_1$–$C_4$)alkyl, which represents a straight or branched alkyl chain having from one to four carbon atoms with a hydroxy group attached to it. Exemplary hydroxy($C_1$–$C_4$)alkyl groups include hydroxymethyl, 2-hydroxyethyl, 3-hydroxypropyl, 2-hydroxyisopropyl, 4-hydroxybutyl and the like.

Yet another substituted alkyl is $C_1$–$C_4$ alkylthio($C_1$–$C_4$)alkyl, which is a straight or branched $C_1$–$C_4$ alkyl group with a $C_1$–$C_4$ alkylthio group attached to it. Exemplary $C_1$–$C_4$ alkylthio($C_1$–$C_4$)alkyl groups include methylthiomethyl, ethylthiomethyl, propylthiopropyl, sec-butylthiomethyl, and the like.

Yet another exemplary substituted alkyl is heterocycle($C_1$–$C_4$)alkyl, which is a straight or branched alkyl chain having from one to four carbon atoms with a heterocycle attached to it. Exemplary heterocycle($C_1$–$C_4$)alkyls include pyrrolylmethyl, quinolinylmethyl, 1-indolylethyl, 2-furylethyl, 3-thien-2-ylpropyl, 1-imidazolylisopropyl, 4-thiazolylbutyl and the like.

Yet another substituted alkyl is aryl($C_1$–$C_4$)alkyl, which is a straight or branched alkyl chain having from one to four carbon atoms with an aryl group attached to it. Exemplary aryl($C_1$–$C_4$)alkyl groups include phenylmethyl, 2-phenylethyl, 3-naphthyl-propyl, 1-naphthylisopropyl, 4-phenylbutyl and the like.

The heterocycloalkyls and heteroaryls can, for example, be substituted with 1, 2 or 3 substituents independently selected from halo, halo($C_1$–$C_4$)alkyl, $C_1$–$C_4$ alkyl, $C_1$–$C_4$ alkoxy, carboxy, $C_1$–$C_4$ alkoxycarbonyl, carbamoyl, N-($C_1$–$C_4$)alkylcarbamoyl, amino, $C_1$–$C_4$alkylamino, di($C_1$–$C_4$)alkylamino or a group having the structure —$(CH_2)_a$—$R^7$ where a is 1, 2, 3 or 4 and $R^7$ is hydroxy, $C_1$–$C_4$ alkoxy, carboxy, $C_1$–$C_4$ alkoxycarbonyl, amino, carbamoyl, $C_1$–$C_4$alkylamino or di($C_1$–$C_4$)alkylamino.

Examples of substituted heterocycloalkyls include, but are not limited to, 3-N-t-butyl carboxamide decahydroisoquinolinyl and 6-N-t-butyl carboxamide octahydro-thieno[3,2-c]pyridinyl. Examples of substituted heteroaryls include, but are not limited to, 3-methylimidazolyl, 3-methoxypyridyl, 4-chloroquinolinyl, 4-aminothiazolyl, 8-methylquinolinyl, 6-chloroquinoxalinyl, 3-ethylpyridyl, 6-methoxybenzimidazolyl, 4-hydroxyfuryl, 4-methylisoquinolinyl, 6,8-dibromoquinolinyl, 4,8-dimethylnaphthyl, 2-methyl-1,2,3,4-tetrahydroisoquinolinyl, N-methyl-quinolin-2-yl, 2-t-butoxycarbonyl-1,2,3,4-isoquinolin-7-yl and the like.

A "pharmaceutically acceptable solvate" is intended to mean a solvate that retains the biological effectiveness and properties of the biologically active components of the inventive compounds.

Examples of pharmaceutically acceptable solvates include, but are not limited to, compounds prepared using water, isopropanol, ethanol, methanol, DMSO, ethyl acetate, acetic acid, or ethanolamine.

In the case of solid formulations, it is understood that the inventive compounds may exist in different forms, such as stable and metastable crystalline forms and isotropic and amorphous forms, all of which are intended to be within the scope of the present invention.

A "pharmaceutically acceptable salt" is intended to mean those salts that retain the biological effectiveness and properties of the free acids and bases and that are not biologically or otherwise undesirable.

Examples of pharmaceutically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxyenzoates, phthalates, sulfonates, xylenesulfonates, phenylacetates, phenylpropionates, phenylbutyrates, citrates, lactates, γ-hydroxybutyrates, glycolates, tartrates, methanesulfonates, propanesulfonates, naphthalene-1-sulfonates, naphthalene-2-sulfonates, and mandelates.

If the inventive compound is a base, the desired salt may be prepared by any suitable method known to the art, including treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, pyranosidyl acids such as glucuronic acid and galacturonic acid, alpha-hydroxy acids such as citric acid and tartaric acid, amino acids such as aspartic acid and glutamic acid, aromatic acids such as benzoic acid and cinnamic acid, sulfonic acids such a p-toluenesulfonic acid or ethanesulfonic acid, or the like.

If the inventive compound is an acid, the desired salt may be prepared by any suitable method known to the art, including treatment of the free acid with an inorganic or organic base, such as an amine (primary, secondary or tertiary), an alkali metal or alkaline earth metal hydroxide or the like. Illustrative examples of suitable salts include organic salts derived from amino acids such as glycine and arginine, ammonia, primary, secondary and tertiary amines, and cyclic amines such as piperidine, morpholine and piperazine, and inorganic salts derived from sodium, calcium, potassium, magnesium, manganese, iron, copper, zinc, aluminum and lithium.

All inventive compounds that contain at least one chiral center may exist as single stereoisomers, racemates and/or mixtures of enantiomers and/or diastereomers. All such single stereoisomers, racemates and mixtures thereof are intended to be within the scope of the present invention. Preferably, the compounds of the present invention are used in a form that contains at least 90% of a single isomer (80% enantiomeric or diastereomeric excess), more preferably at least 95% (90% e.e. or d.e.), even more preferably at least 97.5% (95% e.e. or d.e.), and most preferably at least 99% (98% e.e. or d.e.). Compounds identified herein as single stereoisomers are meant to describe compounds used in a form that contains at least 90% of a single isomer.

Scheme 1

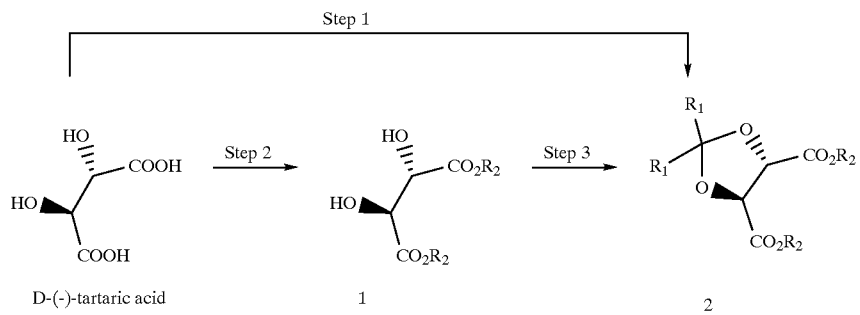

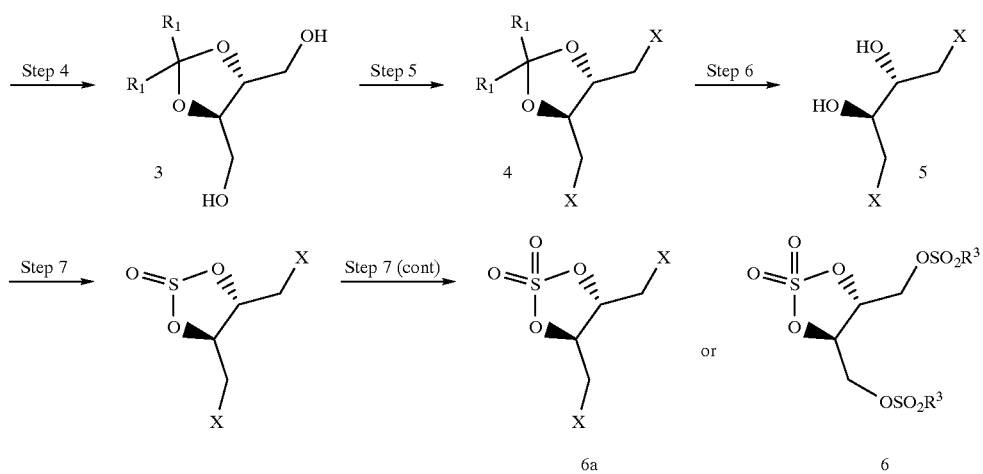

The inventive compounds of general structure 6a can be made from D-tartaric acid via many permutations, as demonstrated in Scheme 1:

First, the conversion of D-tartaric acid to the intermediate of formula 2 can take different pathways. It may be first converted to the compound of formula 1 via Fisher-type esterifications (Step 2) involving refluxing any alcohol in the presence of organic acids such as alkyl or arylsulfonic acids or inorganic acids such as hydrochloric, sulfuric or nitric acids. Compounds of formula 1 are also commercially available from a number of suppliers.

Compounds of formula 1 may then be converted to the protected diester of formula 2 (Step 3) using any of a large variety of acetal or ketal protecting groups. The groups $R_1$ may comprise any acetal or ketal such as an acetonide, cyclohexylidene keta), benzylidene acetal, 2-methoxyethoxyethyl acetal or a related acetal or ketal. Such groups are installed by acid-promoted condensation of the corresponding ketone or aldehyde with the compound of formula 1. These are promoted by both organic acids such as p-toluenesulfonic acid and related alkylsulfonic and arylsulfonic acids, trifluoroacetic acid and related organic carboxylic acids with a pK of less than 2, and inorganic acids such as sulfuric acid, hydrochloric acid, phosphoric acid, and nitric acid.

Alternatively, D-tartaric acid may be converted to compounds of formula 2 in a single reaction vessel (Step 1) by appropriate choice of the esterifying alcohol $R_2$ and the aldehyde or ketone component. Such reactions are modeled after those previously disclosed in the chemical literature (see Mash, E. A.; Nelson, K. A.; Van Deusen, S.; Hemperly, S. B. *Org. Synth. Coll. Vol. VII*, 155,1990).

The reduction of compounds of formula 2 to compounds of formula 3 (Step 4) can be performed using a variety of reducing agents such as $NaBH_4$ in alcoholic media, lithium borohydride or lithium aluminum hydride and related substituted aluminum and boron hydrides in ethereal solvents like THF, diethyl ether, dioxane and MTBE.

The diols of formula 3 can be converted to compounds of formula 4 via a number of methods (Step 5). The leaving group can preferably be any halogen, alkyl or arylsulfonate. The sulfonates can be produced by reaction of the diol with 2 equivalents or greater of the corresponding sulfonyl halides such as p-toluenesulfonyl chloride, methanesulfonyl chloride in the presence of an organic amine base like triethylamine, diethylamine, diethyl isopropylamine, DABCO or related di- or trialkylamines, as well as amidine bases like DBU and DBN. The compounds where X=halogen can be prepared from such sulfonate intermediates by reaction with metal halides such as LiCl or LiBr in dipolar aprotic solvents like dimethylformamide and dimethylsulfoxide. Alternatively the halides may be made directly from the alcohols using classical reagents for this purpose such as $PBr_3$ and $SOCl_2$.

Compounds of the formula 4 may be converted to the diol of formula 5 (Step 6) under aqueous or alcoholic acidic conditions, promoted by Lewis acids such as transition metal halides or halides of the Group 3 metals, or by protic organic acids such as p-toluenesuifonic and related alkyl and arylsulfonic acids, trifluoroacteic acid and related organic carboxylic acids with a pK of less than 6, and inorganic acids such as sulfuric, hydrochloric, phosphoric and nitric acids. Note that compounds of the formula 4 where R and R1 are methyl and R3 is p-toluenesulfonates are commercially available from the Aldrich Chemical Company (see Scheme 2, infra.).

The diol of formula 5 may be converted to the cyclic sulfates of formula 6 and formula 6a (Step 7) using a two stage procedure involving an intermediate cyclic sulfite produced by action of thionyl chloride or thionyl imidazole either neat or in most common organic solvents like halogenated methanes and ethanes, esters and ethers. The reaction may be accompanied by an organic amine base like triethylamine, diethylamine, diethyl isopropylamine, DABCO or related trialkylamines. Oxidation of the intermediate cyclic sulfite to the sulfate of formula 6 is usually performed with a Ru(III) catalyst with the ultimate oxidant being sodium periodate, or sodium or calcium hypochlorites in an aqueous-organic solvent mixture. Alternatively, diol 5 may be converted directly to cyclic sulfate 6 by use of sulfuryl chloride or sulfuryldiimidazole under the same reaction conditions as stated in this paragraph for thionyl chloride and thionyl diimidazole.

The pathways for the production of nelfinavir free base involve the sequence of intermediates shown in Schemes 2 and 3, proceeding via azido-alcohol and phthalimido alcohol intermediates, respectively. The processes both proceed through cyclic sulfate intermediates of formulas 6 and 6a. They diverge after that point and take quite different paths to nelfinavir free base.

Scheme 2
Synthesis of Nelfinavir Free Base from (2S,3S)-(-)-tartaric acid via the Azido Alcohol Route
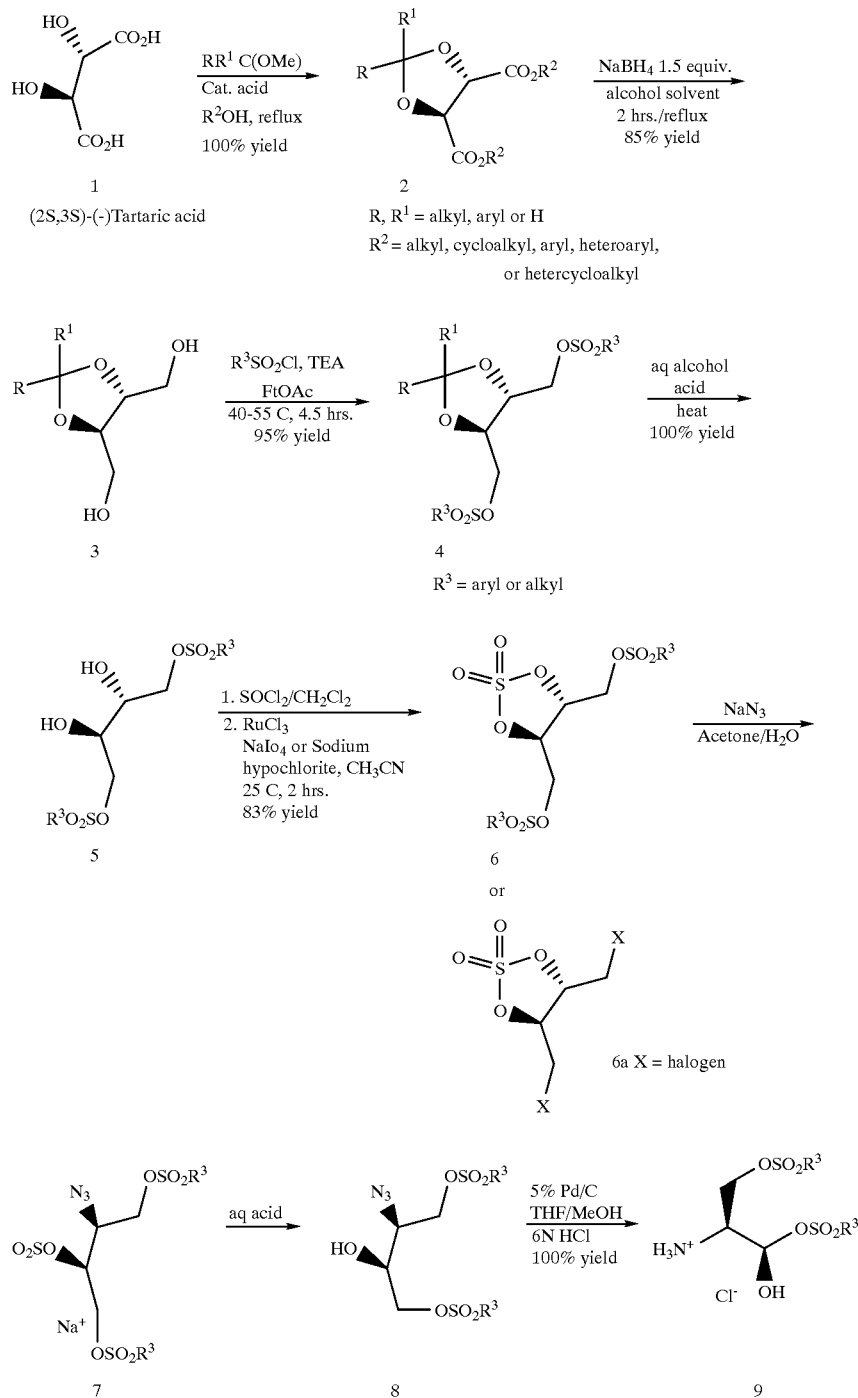

-continued

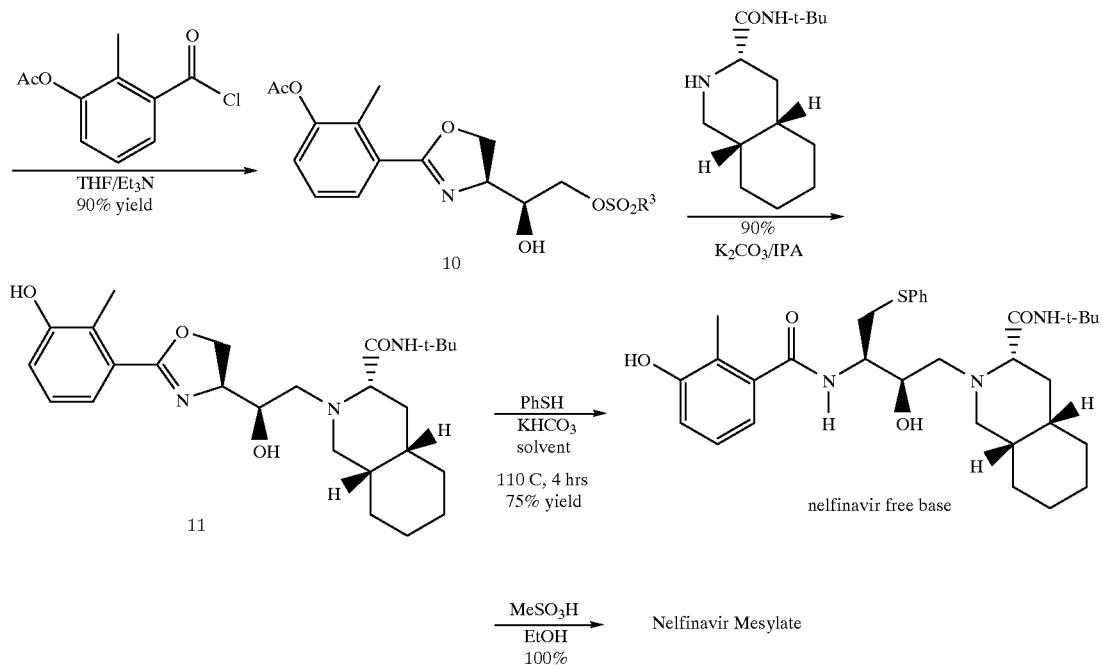

Scheme 2 describes a reaction sequence wherein (2S,3S)-(−)tartaric acid is converted to a cyclic sulfate diaryl or dialkyl sulfonate 6 via reaction transformations such as those detailed above. This reaction scheme involves the conversion of 6 to 8 through 7, in which sodium azide attacks the more labile sulfate functionality exclusively over the primary alkyl or arylsulfonate termini to yield the azido-alcohol adduct 8 in 95% yield. In addition to sodium azide, one may use any inorganic metal azide or an organic tetralkylammonium azide. The solvents for this transformation range from aqueous solutions of polar organic solvents such as acetone, THF, DMF (N,N-dimethylformamide), DMAC (N,N-dimethylacetamide), DMSO or N-methyl-2-pyrollidone at temperatures ranging from 25° C.–70° C., although the preferred conditions are aqueous acetone at 25° C. This reaction can be carried out in a variety of polar organic solvents. Similar chemistry has been extended to the dihalogenated analogs (6a) of 6 as well. Intermediate 6, the corresponding dihalogenated analogs (6a) and ensuing compounds that are indicated in this Scheme have been prepared for the first time and are useful to make nelfinavir free base. To the inventors' knowledge, this is the first example of a nitrogen (or any other) nucleophile selectively reacting with an internal sulfate in the presence of primary carbon centers bearing leaving groups. The sulfate 7 is hydrolyzed off using a strong inorganic protic acid. Typical ideal conditions would include use of sulfuric acid with 1–2 equivalents of water present in a solvent such as THF.

Catalytic hydrogenation of 8 to 9 can be performed with a variety of palladium catalysts such as Pd on carbon, palladium hydroxide and related Pd(II) species at pressures as low as 1 atmosphere and temperatures as low as 25° C. Suitable solvents for this reaction include alcohols of 7 carbons or less, ethyl acetate and related esters of 8 carbons or less, THF and other ethers. A strong protic acid such as HCl, HBr, sulfuric or nitric acid is used. Preferred conditions utilize a mixture of methanol and THF as solvent with 6M HCl present using 5% palladium on carbon catalyst at 1 atmosphere pressure of hydrogen.

Coupling of the amine salt with 3-acetoxy-2-methyl-benzoyl chloride (AMBCl) in the presence of base affords the oxazoline 10 in approximately 90% yield. This compound and methods of making this compound are disclosed in U.S. application Ser. No. 08/708,411, of inventors M. Deason and K. Whitten, titled "Intermediates for Making HIV-Protease Inhibitors and Methods of Making HIV-Protease Inhibitors", filed on Sep. 5, 1996. The coupling may be performed in most common organic solvents such as THF, diethyl ether, dioxane, methyl t-butyl ether or other ethers; esters such as ethyl, methyl and isopropyl acetate, halogenated solvents such as halogenated methanes and ethanes, chlorobenzene and other halogenated benzenes, nitriles such as acetonitrile and propionitrile; lower alcohols such as ethanol, isopropanol, t-butanol and related alcohols, and polar organic solvents such as dimethylformamide, dimethylsulfoxide, N-methyl-2-pyrrollidone and related amide-containing solvents. A base is frequently used and may be any of a number of inorganic bases such as metal hydroxides, bicarbonates and carbonates or organic bases such as amines like triethylamine, diethylamine, diethyl isopropylamine, DABCO (1,4-diazabicyclo[2.2.2]octane) or related di-or trialkylamines, as well as amidine bases such as DBM (1,5-diazabicyclo[4.3.0]non-5-ene) and DBU (1,8-diazabicyclo[5.4.0]undec-7-ene). Preferred conditions have been found to be use of triethylamine in THF at 25° C. for several hours.

Subsequent treatment with base and 3S,4aR,8aR-3-N-t-butylcarboxamido-decahydroisoquinoline (PHIQ, which can be purchased from Procos SpA and NSC Technologies and which can be prepared according to the method described in U.S. Pat. No. 5,256,783, which is incorporated herein by reference) affords 11 quantitatively. Several permutations of base/solvent combinations can be applied to conduct this transformation. The base can be any metal carbonate, bicarbonate or hydroxide in an alcoholic medium such as methanol, ethanol, isopropanol or an analogous alkyl alcohol of 7 or less. The preferred temperatures of the process range from 25–70° C. or at the reflux temperature of the solvent mixture. Preferred conditions involve use of potassium carbonate in isopropanol or methanol at 60° C. for 5–10 hours.

The next step in this Scheme is the reaction of 11 with thiophenoxide which cleaves the oxazoline ring to generate nelfinavir free base. This transformation can be carried out either neat or in any polar organic solvent. Preferred solvents are ketones of greater than 5 carbons, such as cyclohexanone, methyl isobutylketone or ethers such as THF, dioxane and related cyclic or acyclic ethers. A base may be required, and acceptable bases include any methyl carbonate, bicarbonate or hydroxide. The reaction is run generally at or near the reflux temperature of the solvent. Preferred conditions involve the use of excess thiphenol in methyl isobutylketone at reflux with potassium bicarbonate as base.

Cyclic sulfate 6 serves as a common intermediate in both reaction pathways outlined in Schemes 2 and 3. Moreover, in the latter case, the phthalimido alcohol adduct 7a, obtained from the reaction of 6 with potassium phthalimide, serves both as a masked amine and a usefull precursor for the oxazoline ring formation in the next step. This transformation proceeds rapidly in aqueous acetone and DMF (N,N-dimethylformamide), while solvents such as N-methyl-2-pyrrolidone and N,N-dimethylacetamide are also acceptable. Imide bases derived from maleimide and succinimide may function as alternatives to phthalimide in the process. The reaction pathway leading to nelfinavir free base from 7a is significantly different from the azido alcohol route shown in Scheme 2. In Scheme 3, the conversion of 7a to the epoxy oxazoline 8a occurs in the presence of base/ alcohol mixtures, thus delivering the two primary electrophilic sites in the 4-carbon unit with different reactivity profiles. Such base/alcohol combinations may include any alkyl alcohol and any inorganic metal carbonate, bicarbon- Scheme 3
Synthesis of Nelfinavir Free Base from (-)-tartaric acid via the phthalimido alcohol route.

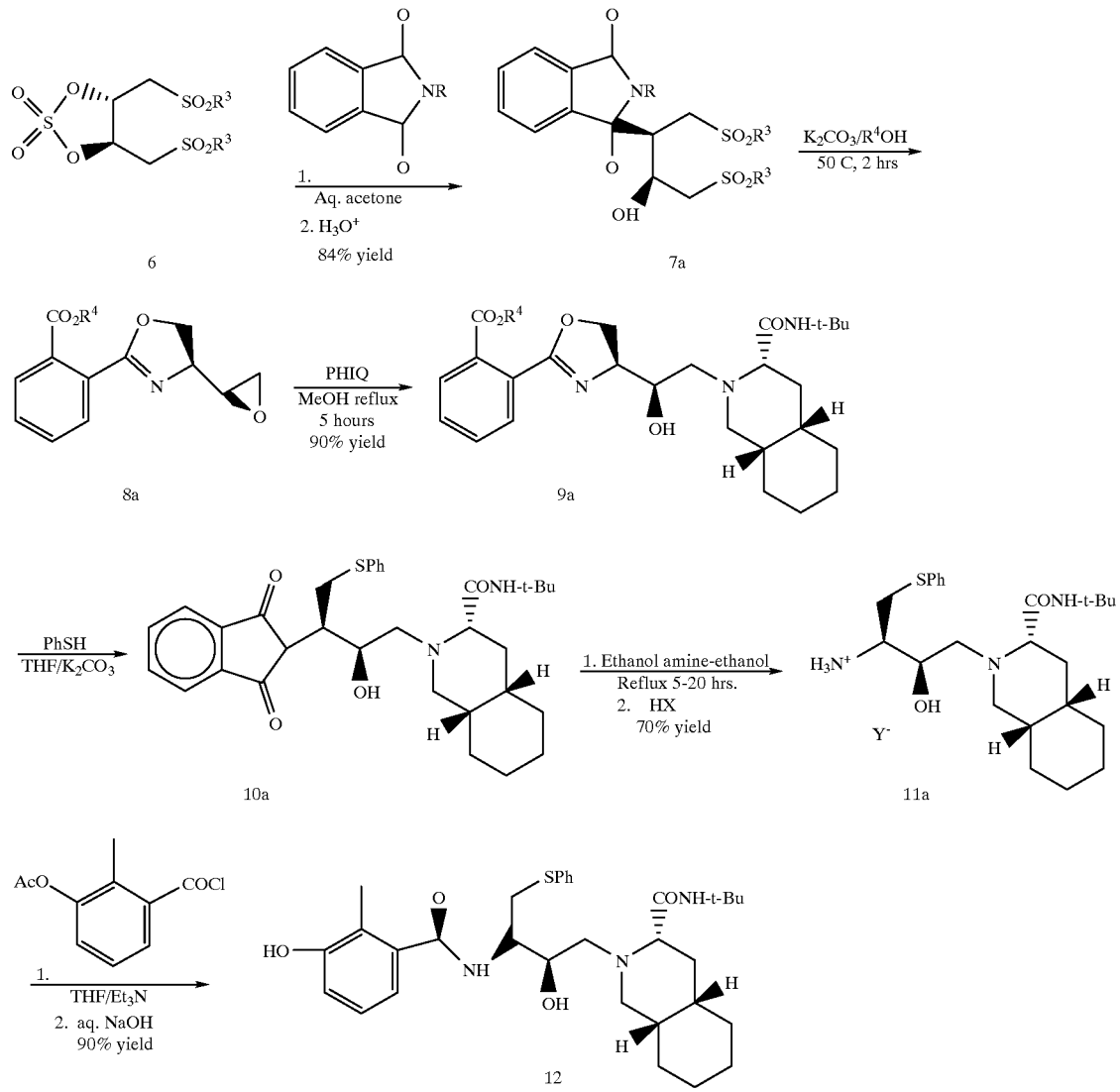

ate or hydroxide. Preferred conditions involve the use of potassium carbonate in methanol. The exact alcohol used will determine the resulting ester functionality produced. Thus, the epoxide terminus in 8a is reacted with PHIQ in the same reaction vessel to afford 9a in approximately 90% yield.

Reaction of 9a with thiophenoxide cleaves the oxazoline ring to generate intermediate 10a. This transformation can be carried out either neat or in any polar organic solvent. Preferred solvents are ketones of greater than 5 carbons such as cyclohexanone, methyl isobutylketone or ethers such as THF, dioxane and related cyclic or acyclic ethers. A base may be required, and acceptable bases include any metal carbonate, bicarbonate or hydroxide. The reaction is run generally at or near the reflux temperature of the solvent. Preferred conditions involve the use of excess thiophenol in THF at reflux with potassium carbonate as base. The resulting isoimide 10a is then hydrolyzed to the free amine of 11a with ethanolamine in 70% overall yield. One can also use hydrazine in alcoholic solvents. 11a can be either isolated as any alkyl or aromatic acid salt, although camphorsulfonic acid and benzoic acid are preferred. The salt 11a or the free base is then coupled with 3-acetoxy-2-methyl benzoyl chloride (AMBCI) to form nelfinavir free base (12). The procedure for this transformation is described in U.S. patent application Ser. No. 08/708,411 of inventors M. Deason and K. Whitten, titled "Intermediates for Making HIV-Protease Inhibitors and Methods of Making HIV-Protease Inhibitors", filed Sep. 5, 1996, the disclosure of which is herein incorporated by reference. Compounds 7a–11a described in this scheme are novel and are useful for preparation of nelfinavir free base.

Since the phthalimido alcohol route intersects at the 11a stage with the chloroalcohol chemistry (described in U.S. patent application Ser. No. 08/708,411 of inventors M. Deason and K. Whitten, titled "Intermediates for Making HIV-Protease Inhibitors and Methods of Making HIV-Protease Inhibitors", filed Sep. 5, 1996) wherein the expensive AMBCI is introduced in the final step, it may be cheaper than the azido alcohol process described earlier. The phthalimido alcohol route may have some advantages over the chloro alcohol route for commercial production.

Experimental Section
I. Procedures for the Tosylate/Azide Version of the Tartaric Acid Route

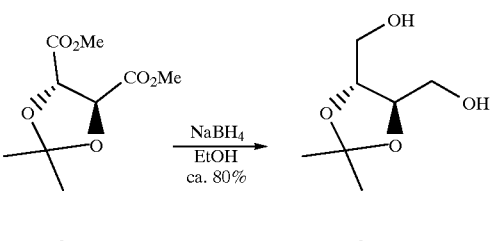

Ref: Mash, E. A.; Nelson, K. A.; Van Deusen, S.; Hemperly, S. B. *Org. Synth. Coll. Vol VII,* 155 (1990).

| Chemical | MW | Density | Scale Factor |
|---|---|---|---|
| D-Tartaric Acid | 150.09 | | 1 equiv. |
| 2,2-dimethoxypropane | 104.15 | .847 | 3.4 equiv. |
| Methanol | 32.14 | .791 | .15 equiv. |
| p-toluenesulfonic acid monohydrate | 190.22 | | .003 equiv. |
| Cyclohexane | 84.16 | .779 | 1 g (1)/4.5 ml |

Into a 5L round bottom flask was placed 505 g (3.36 mol) of D-tartaric acid (Fluka, 98–99% ee), 1425 mL of 2,2-dimethoxypropane, 20 mL of methanol, 2.0 g of TsOH hydrate, and 2250 mL of cyclohexane. The mixture was brought to reflux with stirring and the acetone/cyclohexane and methanol/cyclohexane azeotropes were distilled off slowly at 52–54° C. over a two day period. This was accomplished with a variable takeoff head using a reflux ratio of Ca. 8:1. When the head temperature dropped off, heating was increased to distill off residual 2,2-dimethoxypropane and any remaining cyclohexane. When no more liquid was coming off, heating was stopped and the residual red-orange liquid was analyzed by 1 H NMR. This consisted of almost pure 2. This material could be taken into the reduction without further purification. The $^1$H NMR spectrum indicated identity with the commercial material:

$^1$H NMR (CDCl$_3$) δ 4.8 (s 2H), 3.8 (s, 6H), 1.4 (s, 6H).

| Chemical | MW | Density | Scale Factor | Grade |
|---|---|---|---|---|
| Compound 2 | 218.21 | | 1 equiv. | |
| Sodium Borohydride | 37.83 | | 1.5 equiv. | Aldrich, 98% powder |
| Ethanol | 46.07 | .785 | 1 g (1)/10 ml | McCormick Distilling Co. 200 proof Absolute |
| Methyl t-butyl ether | 88.15 | .740 | | Fisher |
| Sat'd NaCl | | | | |

Reference: Takano, S.; et al; *Synthesis,* 1986, 811.

Procedure:

In a 1 liter 3-neck flask was placed a magnetic stirrer, thermometer and dropping funnel with an Argon purge. The NaBH$_4$ (13.05 g, 0.345 mol) was slurried in 350 ml of ethanol and cooled to 5° C. with an ice bath. Compound 2 (50 g, 0.23 mol) was slurried in 150 ml of ethanol and added dropwise keeping the temperature less than 20° C. The mixture was then stirred at 5–10° C. for 2.5 hours. This was then concentrated on a rotovap to about a third of its volume and a solvent exchange was done with MTBE. The final volume of the solution should be about 500 ml of MTBE. This was then filtered to remove borane salts and washed with 75 ml of saturated NaCl. (The washes should be minimized because of the extreme water solubility of the product). This was then concentrated on a rotovap to give a yellow oil. 24.05 g, 65% yield. (Corrected yield was ~82% based on the starting material containing ~20% of the deprotected diol). This could be taken into the tosylation without further treatment. The $^1$H NMR spectrum indicated identity with the commercial material:

$^1$H NMR (CDCl$_3$) δ 4.0 (br s, 2H), 3.8 (br d, 2H), 3.7 (br d, 2H), 3.6 (br s, 2H), 1.4 (s, 6H).

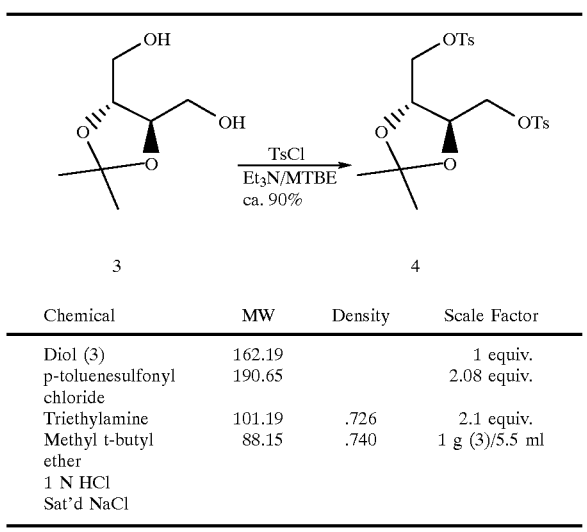

| Chemical | MW | Density | Scale Factor |
|---|---|---|---|
| Diol (3) | 162.19 | | 1 equiv. |
| p-toluenesulfonyl chloride | 190.65 | | 2.08 equiv. |
| Triethylamine | 101.19 | .726 | 2.1 equiv. |
| Methyl t-butyl ether | 88.15 | .740 | 1 g (3)/5.5 ml |
| 1 N HCl | | | |
| Sat'd NaCl | | | |

Reference: *J. Org. Chem.* 1980, 45, 2995.

Procedure:

The diol (351 g, 2.16 mol) was dissolved in 2.0L of MTBE and Et$_3$N (640 ml, 466 g, 4.60 mol) was added. The TsCl (860 g, 4.51 mol, 2.08 equiv) was added as a solid in portions keeping the temperature under 40° C. The mixture was stirred for 17 hours after the end of the addition. TLC analysis can be accomplished with CH$_2$Cl$_2$/EtOAc (70:30) with PMA development. The diol (R$_f$=0.10), monotosylate (R$_f$=0.0.45) and ditosylate (R$_f$=0.88) are easily observed during the course of the reaction. The reaction mixture was washed successively with water (2×2.0L), 1N HCl (1×1.0L) and brine (1×1.0L). The layer was dried with Na$_2$SO$_4$ and evaporated to leave an orange oil (873 g, 85%). This was analyzed by $^1$H NMR and showed the ditosylate contaminated with ca 10% TsCl. This could be taken directly into the hydrolysis reaction without further purification. The $^1$H NMR spectrum indicated identity with the commercial material:

$^1$H NMR (CDCl$_3$) δ 7.8 (d, 4H), 7.4 (d, 4H), 4.2–4.0 (overlapping m, 6H), 2.4 (s, 6H), 1.2 (s, 6H).

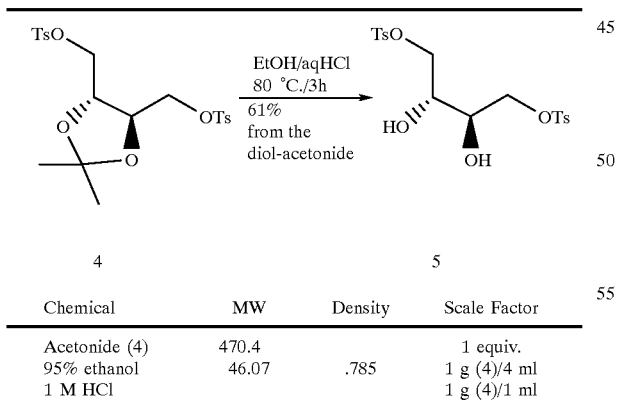

| Chemical | MW | Density | Scale Factor |
|---|---|---|---|
| Acetonide (4) | 470.4 | | 1 equiv. |
| 95% ethanol | 46.07 | .785 | 1 g (4)/4 ml |
| 1 M HCl | | | 1 g (4)/1 ml |

Procedure:

The crude acetonide from the previous step (ca. 873 g) was dissolved in 4 volumes of 95% ethanol and 1 volume of 1M HCl was added. The mixture was heated to reflux for 3 hours. Evaporation of a small aliquot of the solution and analysis by $^1$H NMR showed the reaction to be complete. Two workups may be used. The solvents may be evaporated to give the product directly which shows no other organic products by $^1$H NMR except solvent. This is usually contaminated with EtOH and water, however. Alternatively, the bulk of the solvent may be removed by rotary evaporation and the remainder extracted with EtOAc (two times). The combined extracts were washed with water and brine and dried with Na$_2$SO$_4$. The drying agent was filtered off and the solvent removed by rotary evaporation to give 571 g of a dark tan gray solid (61% from diol-acetonide). $^1$H NMR showed the ditosylate diol contaminated with a small amount of EtOAc. This was used directly in the next step. The $^1$H NMR spectrum indicated identity with the commercial material:

$^1$H NMR (CDCl$_3$) δ 7.8 (d, 4H), 7.4 (d, 4H), 4.1 (m, 4H), 3.9 (app t, 2H), 3.0 (br s, 2H), 2.4 (s, 6H).

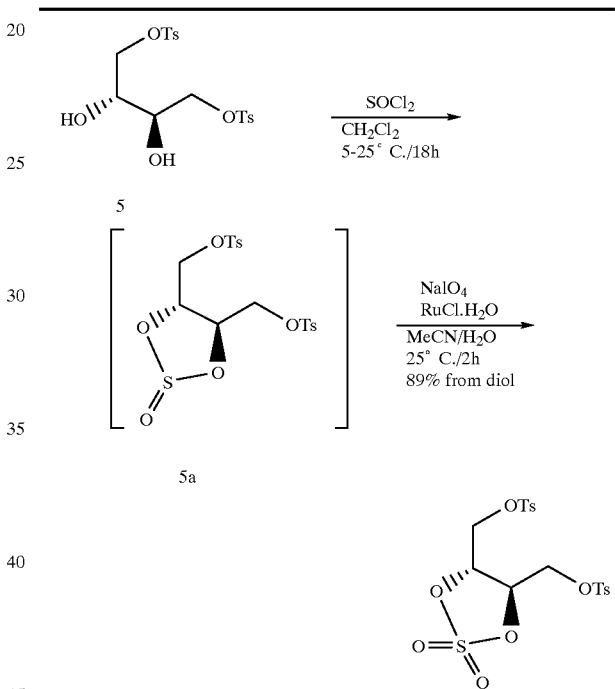

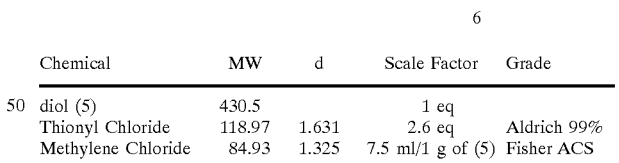

| Chemical | MW | d | Scale Factor | Grade |
|---|---|---|---|---|
| diol (5) | 430.5 | | 1 eq | |
| Thionyl Chloride | 118.97 | 1.631 | 2.6 eq | Aldrich 99% |
| Methylene Chloride | 84.93 | 1.325 | 7.5 ml/1 g of (5) | Fisher ACS |

Procedure:

In a 2 liter, 3-neck flask was placed the diol 5 (100 g, 0.23 mol) and 750 mL of methylene chloride. This was cooled to 5° C. with an ice bath and purged with argon. The thionyl chloride (71.2 g, 44 ml, 0.6 mol) was added dropwise and the mixture then allowed to warm to room temperature overnight (18 hours). Gas evolution was seen throughout. The mixture was then concentrated on a rotovap to yield 105.5 g of brown oil (96% yield). The reaction can be followed by (TLC: 20% EtOAc/CH$_2$Cl$_2$: SiO$_2$). This material can be used as is in the next step.

| Chemical | MW | d | Scale Factor | Grade |
|---|---|---|---|---|
| Compound (5a) | 476.5 | | 1 eq | |
| Ruthenium III Chloride hydrate | 207.42 | | 1 mg/5 g of 5a | Aldrich |
| Sodium Periodate | 213.89 | | 1.5 eq | Aldrich 99% |
| Acetonitrile | 41.05 | .786 | 4 ml/g of (5a) | Fisher ACS |
| Deionized water | 18 | 1 | 10 ml/g of (5a) | Deionized |

Procedure:

In a 3 liter, 3-neck flask was placed the sulfite 5a (105.5 g, 0.22 mol) with 400 mL acetonitrile and 1000 mL D. I. Water. This formed a biphasic mixture of oil and solvent. The ruthenium (III) chloride (20 mg) was added and the mixture stirred under argon. The sodium periodate (67.4 g, 0.32 mol) was added in four equal portions. No exotherm was seen after the addition. This mixture was stirred at room temperature for two hours and product slowly crystallized from the reaction mixture. This was filtered and dried overnight at 50° C. in a vacuum oven. Yield: 94.6 g of tan solid (87% yield). The filtrate was extracted with methyl-t-butyl ether and concentrated to give an additional 6 g of material for an overall yield of 93%.

$^1$H NMR (CDCl$_3$) δ 7.8 (d, 4H), 7.4 (d, 4H), 5.0 (m, 2H), 4.4 (m, 4H), 3.0 (br s, 2H), 2.5 (s, 6H).

| Chemical | MW | Density | Scale Factor |
|---|---|---|---|
| Cyclic Sulfate (6) | 492.5 | | 1 equiv. |
| Sodium azide | 65.01 | | 1.15 equiv. |
| Acetone | 58.08 | .791 | 1 g (6)/5 ml |
| DI Water | 18 | 1 | 1 g (6)/.8 ml |

Procedure:

The cyclic sulfate (545.4 g, 1.10 moles) was dissolved in 2500 mL of acetone and 500 mL of water (no ppt present). While stirring at ambient temperature, sodium azide (1.21 moles, 1.1 equiv, 78.6 g) was added in four portions over 10 minutes. No temperature rise was observed. The reaction was followed by HPLC. After 24 hours, HPLC indicated that the reaction contained 5% starting material and a single major product. Another 5 g of NaN$_3$ was added and the reaction was allowed to stir another 18 hours. HPLC analysis at this time showed the starting material to be consumed resulting in an orange solution. The bulk of the solvent was removed in vacuo and a white solid crystallized from an orange oil. This water-wet cake was carefully removed from the flask and was filtered, washed with water (ca 1L) and pressed dry on the Buchner funnel with gooch rubber. This gave 955.6 g of a wet solid (expect 613.3 g). This was used directly in the next step.

| Chemical | MW | Density | Scale Factor |
|---|---|---|---|
| Azidosulfate (7) | 557.54 | | 1 equiv. |
| DI Water | 18 | 1 | 1 equiv. |
| Sulfuric Acid | | | ~.02 ml/g (7) |
| Tetrahydrofuran | 72.11 | .889 | 1 g (7)/10 ml |
| 5% Pd/C | | | ~.1 g/g (7) |
| Methanol | 32.14 | .791 | 1 g (7)/10 ml |
| 6 N HCl | | | 3 equiv. |

Procedure:

This cake was dissolved in 2200 mL of THF and 0.5 mL of concentrated sulfuric acid was added. The mixture turned slightly turbid. No precipitate and no heat evolution were noted. HPLC analysis indicated no reaction at all after 1 hour. Eight mL of conc. sulfuric acid was added and the mixture was allowed to stir for 18 hours at ambient temperature. HPLC analysis at this time showed ca 40: 60 SM/hydrolysis product and about 200 mL of water had separated from the reaction which was removed. The mixture was filtered through 750 g of sodium sulfate and another 5 mL of sulfuric acid was added. After a total reaction time of 43 h, HPLC analysis showed no sulfate. Extractive workup of a small aliquot showed only the azido alcohol and no sulfate.

The solution was diluted with 2200 mL of methanol, 500 mL of 6N HCl and 50 g of 5% Pd on activated carbon in a 12L glass reactor. Hydrogen gas was bubbled slowly through the solution for 18 hours, TLC analysis (EtOAc/ CH$_2$Cl$_2$ 10:90) showed a trace of azide so the reaction was allowed to stir another 20 hours. The mixture was filtered through a bed of celite on a sintered glass funnel, and washed through with 1.5L of THF to give a bright yellow solution. This was evaporated to provide a very wet gooey oil. This was dissolved in 3L of EtOAc and washed with 500 mL of water and 500 mL of brine. The solution was dried with Na$_2$SO$_4$ and evaporated to give 464.0 g of a light brown oil. This was analyzed by $^1$H NMR and determined to be contaminated with 7% EtOAc. It was assumed that the mixture contained 431 g of the amine salt.

$^1$H NMR (CD$_3$OD) δ 7.8 (overlapping d, 4H), 7.5 (overlapping d, 4H), 4.3 (dd, 1H), 4.2–4.0 (overlapping m, 4H), 3.6 (m, 1H), 2.6 (s, 6H); high resolution mass spectrum calcd for C$_{18}$H$_{24}$NO$_7$S$_2$ 430.0994, found 430.0983.

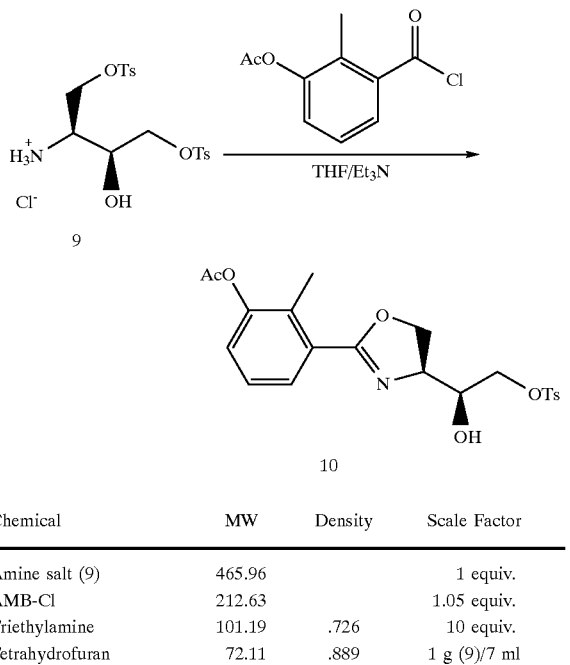

| Chemical | MW | Density | Scale Factor |
| --- | --- | --- | --- |
| Amine salt (9) | 465.96 | | 1 equiv. |
| AMB-Cl | 212.63 | | 1.05 equiv. |
| Triethylamine | 101.19 | .726 | 10 equiv. |
| Tetrahydrofuran | 72.11 | .889 | 1 g (9)/7 ml |

Procedure:

This oil was dissolved in 3.0L of THF and cooled to 9° C. under Ar. The AMB-Cl (206.7 g, 0.97 mol, 1.05 equiv) was added as a liquid. A solution of 1000 mL (ca 10 equiv) of Et$_3$N in 600 mL of THF was added via an addition funnel slowly, observing the temperature. The internal temperature rose to 25° C. over the addition of the first 300 mL of solution (ca the first 1.5 equiv) before subsiding. The remainder of the solution was added rapidly over 20 min to give a tan solution containing a precipitate of triethylamine hydrochloride. The cooling bath was removed and the mixture was stirred at ambient temperature for 16 hours. Workup of a small aliquot of the solution showed no SM and a clean conversion to the oxazoline. The bulk of the solvent was removed in vacuo and the residue was dissolved in 2L of EtOAc and washed successively with water, saturated aq. NaHCO$_3$ (1L), water (1L) and brine (1L). The solution was dried with Na$_2$SO$_4$ and evaporated to give the hydroxytosylate as an orange oil.

$^1$H NMR (CDCl$_3$) δ 7.8 (d, 4H), 7.6 (d, 2H), 7.4 (d, 4H), 7.2 (t, 1H), 7.1 (d, 1H), 4.4–4.2 (overlapping m, 4H), 4.1 (dd, 1H), 3.m, 1H), 2.5 (s, 3H), 2.4 (s, 3H), 2.3 (s, 3H); high resolution mass spectrum calcd for C$_{21}$H$_{23}$NO$_7$S+Cs 566.0250, found 566.0275.

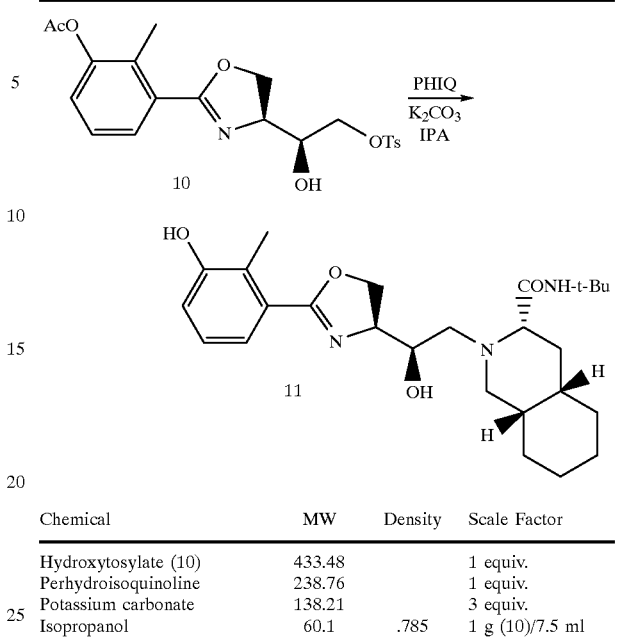

| Chemical | MW | Density | Scale Factor |
| --- | --- | --- | --- |
| Hydroxytosylate (10) | 433.48 | | 1 equiv. |
| Perhydroisoquinoline | 238.76 | | 1 equiv. |
| Potassium carbonate | 138.21 | | 3 equiv. |
| Isopropanol | 60.1 | .785 | 1 g (10)/7.5 ml |

Procedure:

The hydroxytosylate 10 was dissolved in 175 mL of IPA along with 12.50 g (52.3 mmol of PHIQ, ca. 1.0 equiv) of PHIQ and 159 mmol (3 equiv) of K$_2$CO$_3$. The mixture was heated to 70° C. and stirred for 20 hours. A thick white precipitate slowly comes out of the reaction mixture. TLC analysis at this time (methylene chloride/EtOAc 70:30) does not show epoxide or hydroxytosylate, but only a baseline streak/spot. The bulk of the IPA was removed in vacuo and the residue was transferred to 300 mL of water and the pH was brought to ca 7–8 with 6N HCl. The mixture was stirred for 30 min and filtered. The resulting white solid was washed well with water and dried under vacuum to leave 19.0 g (68% from azido-sulfate) of the PHIQ adduct 11 as an off-white solid. This crude substance is identical with that produced by another route. The crude product was slurried in a mixture of 180 mL of methanol and 3675 mL of water and heated to 40° C. for 1 h. The solid was filtered at 40° C. and washed with 500 mL of water. The wet cake was recharged to the reactor and slurried with 3L of water and 300 mL of methanol and heated to 58° C. The mixture was cooled to ca 50° C. and filtered. The filter cake was washed with 1L of water followed by 1L of n—BuOAc. The solid was dried at ca. 28 in Hg to give 215.7 g of 11 which 91.3% pure as assayed by HPLC.

$^1$H NMR (DMSOd$_6$) δ 9.6 (br s, 1H), 7.4 (br s, 1H), 7.2–7.0 (overlapping m, 2H), 6.9 (d, 1H), 4.8 (br s, 1H), 4.5 (m, 1H), 4.3 (app t, 1H), 4.2 (app t, 1H), 3.8 (m, 1H), 2.9 (br d, 1H), 2.6 (br d, 1H), 2.4–1.4 (overlapping m, 15H), 2.4 (s, 3H), 1.2 (s, 9H); 13C NMR (DMSOd$_6$) d 173.6, 164.3, 156.5, 130.1, 126.5, 125.2, 120.9, 117.3, 70.5, 70.4, 70.2, 67.9, 60.1, 59.5, 50.8, 36.5, 34.0, 31.5, 31.0, 29.8, 26.9, 26.5, 21.0, 14.0; high resolution mass spectrum calcd for C$_{25}$H$_{40}$N$_3$O4 (M+H$^+$) 458.3019, found 458.3008.

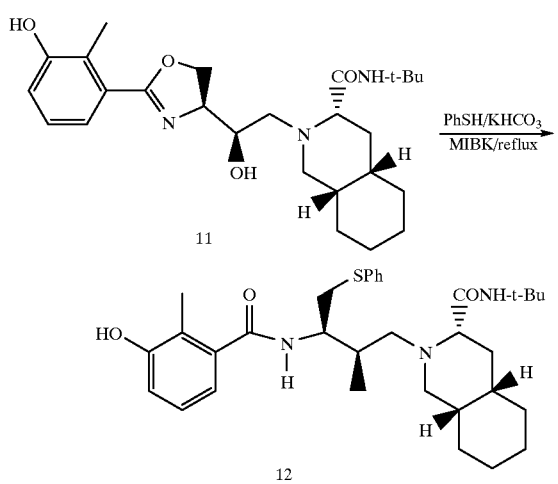

Procedure:

Compound 11 (215 g, 1.0 equiv) was slurried in 1720 mL of MIBK along with KHCO₃ (94.1 g, 2.0 equiv) and thiophenol (193 mL, 4.0 equiv). The mixture was sparged with nitrogen for 2 minutes and then heated to reflux for 6.5 hours with a slow sparge. Toluene was added (1720 mL) and the mixture was refluxed for 1 hour and then slowly allowed to cool to ambient temperature over 5.5 hours. The mixture was filtered and washed with 860 mL of toluene. The solid was dried at ca. 28 in Hg and 55–60° C. overnight to give 317 g of crude compound 12. This was slurried in 2377 mL each of acetone and water and the mixture was heated to ca. 60° C. for 2.5 hours. The mixture was allowed to cool to ambient temperature slowly and filtered. The cake was washed with a mixture of 850 mL of acetone and 850 mL of water and dried at 55–60° C. for 24 hours to give 215 g of purified compound 12. The substance was assayed at 98% purity by HPLC and gave a ¹H NMR spectrum identical to material prepared via another route.

II. Procedures for the Tosylate/Phthalimide Version of the Tartaric Acid Route
Process for the Preparation of the Phthalimido alcohol (7a):

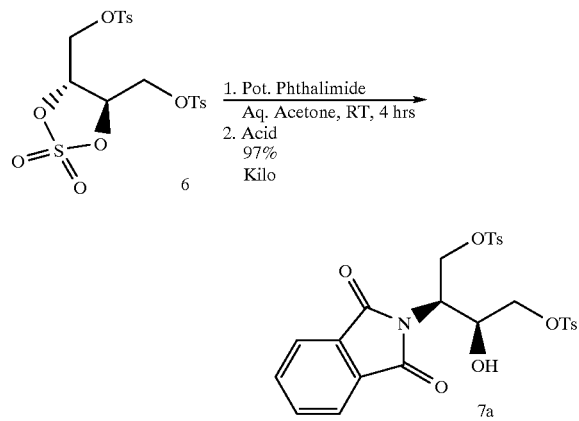

| Raw Material | Source | Amount | M. wt | Mol. |
|---|---|---|---|---|
| Cyclic Sulfate (6) | 991-116-1 | 1100 g | 492.5 | 2.23 |
| Potassium Phthalimide | Aldrich | 455 g | 185.2 | 2.46 |

| | | | | |
|---|---|---|---|---|
| Con. Sulfuric acid | Fisher | 66 mL | — | — |
| Acetone | Fisher | 5.5 L | — | — |
| Water | Stock | 11 L + 198 mL | — | — |

Compound 6, potassium phthalimide, acetone and 198 mL water were charged in a 22L reactor and stirred. An exotherm was observed (35–40° C.). The mixture was stirred for 4 hours as the exotherm subsided. The mixture was checked by HPLC for reaction completion (3 drops of reaction mixture were diluted with 25 volumes of acetonitrile and 0.1M ammonium acetate solution). The mixture was warmed to 50° C. 66 mL of concentrated sulfuric acid were added over 10 minutes. The mixture was sampled to confirm completion of hydrolysis by HPLC as above. Copious amounts of precipitate (potassium sulfate) were observed.

The reaction was held at 50–55° C. for 20 minutes. 5.5L of water were rapidly added over 5 minutes and agitation was increased. 5.5L of more water were added over 1 hour. The temperature rose to 37° C. The product was seen falling out of solution. The product was cooled to 25° C. over 1 hour, and then held for one hour or allowed stir overnight. The solid was filtered and rinsed with water. The cake was dried in a vacuum (29 in Hg) oven at 35° C. overnight or until the water content was below 1%. The yield of 7a was 1205 g (96.6%); HPLC purity 92.9%.

¹H NMR (CDCl₃) δ 7.87–7.83 (m, 1H), 7.79–7.74 ( m, 3H), 7.70 (d, J=8.1 Hz, 2H), 7.62 (d, J=8.1 Hz, 2H), 7.26 (d, J=8.1 Hz, 2H), 7.16 (d, J=8.1 Hz, 2H), 4.63 (app t, J=9.2 Hz, 1H), 4.55–4.39 (m, 3H), 4.06 (dd, J=3.7, 10.7 Hz, 1H), 3.96 (dd, J=4.4, 10.7 Hz, 1H), 3.40 (br s, 1H), 2.38 (s, 3H), 2.25 (s, 3H); high resolution mass spectrum calcd for C₂₆H₂₅NO₉S₂+Cs 692.0025, found 692.0036.

Process for the Preparation of 9a

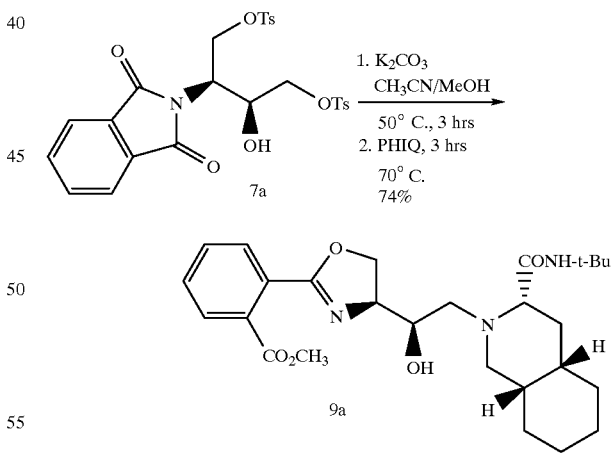

| Raw Material | Source | Amount | M. Wt. | Mol |
|---|---|---|---|---|
| 7a (88% pure) | JDS-4-128 | 1000 g | 559.6 | 1.787 |
| Anh. Potassium carbonate | Fisher | 493.9 g | 138.2 | 3.574 |
| Acetonitrile | Fisher | 2 L | — | — |
| Methanol | Fisher | 4 L | — | — |
| PHIQ | 1252 | 425 g | 238 | 1.787 |
| Water | stock | 10 L | — | — |

Compound 7a, potassium carbonate, 2L acetonitrile and 3L methanol were charged in a 22L reactor. The mixture was stirred, warmed to 50° C., held for 3 hours, then sampled for HPLC analysis (3 drops of the reaction mixture were diluted with 25 drops of 1:1 acetonitrile and 0.1M ammonium acetate solution). The profile consisted of 63% epoxyoxazoline intermediate 8a and <5% starting material. PHIQ dissolved in 1L methanol was added and the batch temperature was raised to 60° C. The mixture was held at this temperature for 3 hours. HPLC analysis showed nearly 70% of product at this stage. 5L water were added over 1–2 minutes, and the heat was removed. The batch temperature was around 40° C. 5L water were added over 1 hour to the mixture, which was cooled to room temperature then held for 1 hour at the temperature. The reaction mixture was then filtered, and the cake was rinsed with 1.5L water and dried in an oven at 50° C. overnight. The yield of 9a was 577 g (74%). The HPLC purity exceeded 99%.

$^1$H NMR (CDCl$_3$) δ 7.79 (d, J=7 Hz, 1H), 7.65 (d, J=7 Hz, 1H), 7.56–7.48 (m, 2H), 5.99 (br s, 1H), 4.50–4.43 (m, 3H), 3.89 (s, 3H), 3.28 (s, 1H), 3.04 (d, J=11.4 Hz, 1H), 2.59–2.51 (m, 2H), 2.34–2.23 (m, 2H), 1.93 ( app q, J=12.9 Hz, 1H), 1.87–1.59 (overlapping m, h.), 1.53–1.15 (overlapping m, 6H), 1.36 (s, 9H); high resolution mass spectrum calcd for C$_{27}$H$_{39}$N$_3$O$_5$+Cs 618.1944, found 618.1956.

Process for the Preparation of Compound 11a

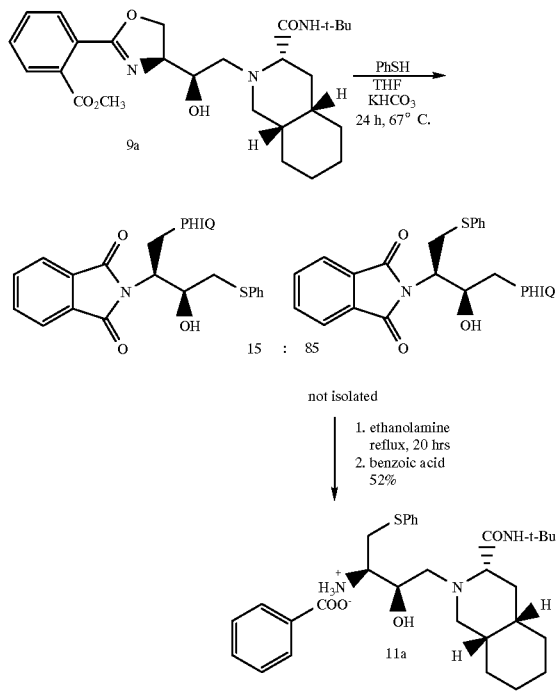

| Raw Material | Source | Amount | M. wt | Mol. |
|---|---|---|---|---|
| 9a | 1183-011 JDS-4-147 | 1000 g | 485.6 | 2.059 |
| Thiophenol | Aldrich | 906 g (844 mL) | 110.0 | 8.237 |
| THF | Fisher | 6 L | — | — |
| Anh. Potassium-bicarbonate | Fisher | 63 g | 100.1 | 0.630 |
| Ethanolamine | Aldrich | 2.12 L | 61 | 34.75 |
| Methyl-t-butylether (MTBE) | Fisher | 9 L | — | — |
| Benzoic acid | Aldrich | 502 g | 122 | 4.11 |

-continued

| | | | | |
|---|---|---|---|---|
| Satd. Bicarbonate soln. | 5 L | — | — | — |
| Hexanes | Fisher | 2.8 L | — | — |

Compound 9a, potassium bicarbonate and 6L THF were charged in a 22L reactor and the mixture was degased with a subsurface argon purge and stirring. Thiophenol was charged in one portion and sparging was continued for 20 minutes. The batch was brought to reflux (67° C.), held at reflux for 26 hours, then sampled for HPLC analysis. The two intermediate isoimides were produced in an ~85:15 in ratio along with 10% unreacted starting material. All of the ethanolamine was charged in one portion, and reflux was continued for 20 hours. The batch was checked by HPLC and cooled to 45° C. 5L of MTBE and 5L of saturated sodium bicarbonate solution were added. The mixture was agitated for 30 minutes and allowed to settle. The layers were separated. The aqueous layer was reextracted with 3L MTBE, and the organics were combined. The MTBE extracts were washed with 5L sodium bicarbonate solution, and the organic layer was separated. The aqueous layer was checked by HPLC for the presence of Compound 10a. 60% of the volatiles were stripped (based on earlier experiments, full stripping of all solvents was warranted since the THF present in this concentrate severely impedes crystallization), and the concentrates were warmed to 50° C. Benzoic acid was added in one portion. The mixture was held for 1 hour. A few seed crystals were added to induce precipitation, and 2.8L hexanes were added. The mixture was cooled to room temperature and held for 1 hour. All of the solid was filtered, and the cake was rinsed with 1L MTBE. The mother liquor was concentrated to an oil, 2L MTBE were added, the mixture was warmed to 50° C. temperature, and then cooled to room temperature, and the product was filtered. This process was repeated with the filtrate. All solids were combined and dried in a vacuum oven at 50° C. overnight. The filtrate still contained 15–20% Compound 10a that could not be derivatized as solid. The yield of 11a was 602 g (52%; note that a 71% yield has been achieved on a similar run conducted on a 200 g scale). The HPLC purity of the product exceeded 99%.

$^1$H NMR (CD$_3$OD) δ 7.97 (d, J=8 Hz, 2H), 7.56 (d, J=8 Hz, 2H), 7.5–7.1 (overlapping m, 6H), 3.77 (m, 2H), 3.10 (m, 1H), 2.96 (m, 2H), 2.74 (d, J=8.5 Hz, 1H), 2.51 (t, J=12.5 Hz, 1H), 2.36 (dd, J=2.5, 13 Hz, 1H), 2.26 ( d, J=11.5 Hz, 1H), 2.02 (q, J=2.5, 13 Hz, 1h), 2.0–1.2 (overlapping m, 12H), 1.31 (s, 9H).

Process for the preparation of Nelfinavir Free Base:

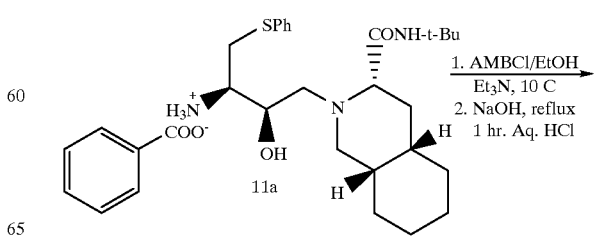

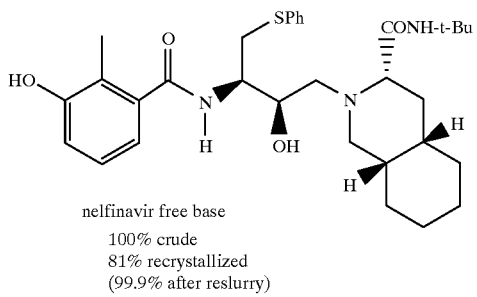

nelfinavir free base
100% crude
81% recrystallized
(99.9% after reslurry)

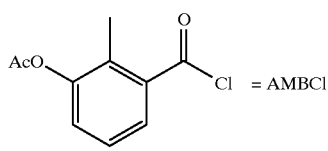

| Raw Material | Source | Amount | M. wt. | Mol. |
| --- | --- | --- | --- | --- |
| 11a | 1183-106 | 600 g | 555.4 | 1.08 |
| Anh. Ethanol | Fisher | 3 L | — | — |
| AMBCl | AB | 252.6 | 212.6 | 1.19 |
| Triethylamine | Aldrich | 327.8 | 101.2 | 3.24 |
| THF | Fisher | 300 mL | — | — |
| 50% NaOH | Fisher | 432 g | 40 | 5.40 |
| Methanol | Fisher | 600 mL | — | — |
| 2.5% Hcl | Stock | 8 L | 36.5 | 5.47 |
| Acetone | Fisher | 9.25 L | — | — |
| Water | Stock | 3 L | — | — |
| 2:1 acetone water | Stock | 3 L | — | — |

11a was slurried in 3L ethanol and cooled to 0° C. Triethylamine was charged in one portion, with the temperature kept below 10° C. AMBCl dissolved in 300 mL THF was charged, with the pot temperature kept below 15° C. The mixture was warmed to room temperature and checked by HPLC to confirm consumption of all of compound of the formula 11a (less than 2% of 11a remained before proceeding with the next operation). 50% NaOH was charged in one portion, and the batch was brought to reflux (75° C.). 600 mL of methanol were added to dilute the mixture. The mixture was sampled by HPLC to confirm completion of hydrolysis. The batch was cooled to room temperature. The slurry was slowly fed in a 22L reactor containing 8L of 2.5% HCl with vigorous agitation. The pH of this slurry was adjusted to between 5 and 6. The batch was warmed to 55° C. and held at this temperature for one hour and filtered hot. The cake was rinsed with water. HPLC analysis of the filtrate indicated mostly benzoic acid with very little nelfinavir free base. The wet cake was dried in a vacuum oven at 65° C. overnight. The yield of crude nelfinavir free base was 1.45 Kg (100%; note that the batch was still 45–55% water wet and contained 1.1% benzoic acid and some inorganic salts).

Crystallization of Nelfinavir Free Base:

A portion of the wet cake (~500 g net AG 1346) was combined with 8.25L acetone and 1.1L water. It was heated to reflux. To this was added 1L acetone and 1L water. The hot mixture was filtered through celite. The filtrate was cooled to room temperature and then to 3° C. and held for one hour. The mixture was filtered and the cake was rinsed with 3L 2.1 acetone/water. The cake was dried in a vacuum oven at 70° C. overnight. The yield of nelfinavir free base was 416 g (81%). HPLC analysis indicated the purity to be 99.4%, but still containing 0.52% benzoic acid.

Reslurry of Nelfinavir Free Base:

The above solid was slurried in 4L water (pH ~4.92). To this was added 1.9 g of 50% NaOH (pH is now 11.8). To this was added 27 mL of 2.5% HC to adjust the pH to between 7.5 and 8. This was heated to 60° C. and held one hour and filtered hot. The cake was rinsed with warm (40° C.) water. The cake was dried in a vacuum oven at 70° C. The yield was 386 g (98%). The filtrate contained mostly benzoic acid with very little nelfinavir free base. HPLC analysis indicated a purity of >99.9% with less than 0.1% benzoic acid. This material was spectroscopically identical to material prepared via other routes.

While the invention has been described in terms of various preferred embodiments using specific examples, those skilled in the art will recognize that various changes and modifications can be made without departing from the spirit and scope of the invention, as defined in the appended claims.

We claim:

1. A synthetic process, comprising converting a compound of formula 7a:

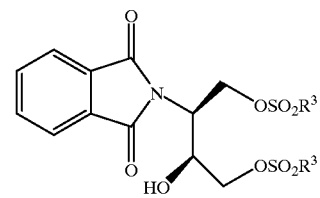

7a wherein each $R^3$ is independently an aryl group or an alkyl group, to a compound of formula 8a:

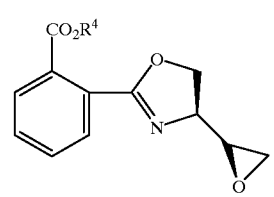

8a wherein $R^4$ is an alkyl group.

2. A process according to claim 1, further comprising converting a compound of formula 6:

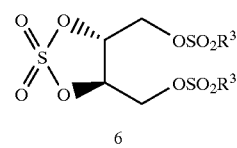

6 wherein each $R^3$ is independently an aryl group or an alkyl group, to form the compound of formula 7a.

3. A process according to claim 2, further comprising converting a compound of formula 5:

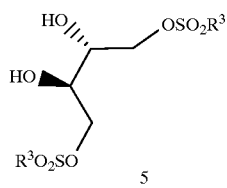

5 wherein each R³ is independently an aryl group or an alkyl group, to form the compound of formula 6.

4. A process according to claim 3, further comprising converting a compound of formula 4:

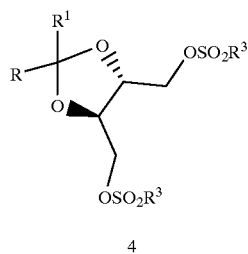

4 wherein each R³ is independently an aryl group or an alkyl group, to form the compound of formula 5.

5. A process according to claim 4, further comprising converting a compound of formula 3:

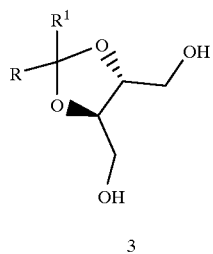

3 wherein R and R¹ each is independently H, an alkyl group, or an aryl group, to form the compound of formula 4.

6. A process according to claim 5, further comprising converting a compound of formula 1:

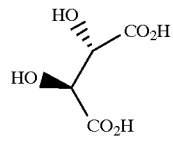

1 to a compound of formula 2:

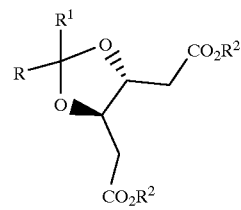

2 wherein R and R¹ each is independently H, an alkyl group, or an aryl group, and each R² is independently an alkyl group, a cycloalkyl group, an aryl group, a heteroaryl group, or a heterocycloalkyl group, and converting the compound of formula 2 to the compound of formula 3.

7. A process according to claim 1, further comprising converting a compound of formula 6a:

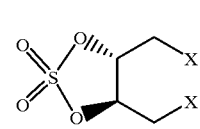

6a wherein each X is independently a halogen, to form the compound of formula 7a.

8. A process according to claim 7, further comprising converting a compound of formula 5:

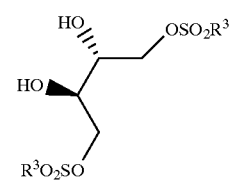

5 wherein each R³ is independently an aryl group or an alkyl group, to form the compound of formula 6a.

9. A process according to claim 1, further comprising converting the compound of formula 8a to a compound of formula 9a:

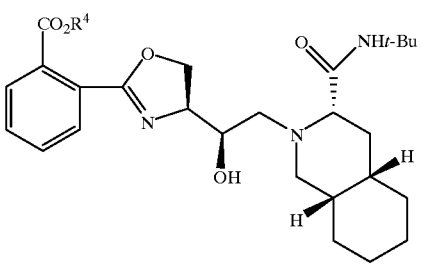

9a wherein R⁴ is an alkyl group.

10. A process according to claim 9, further comprising converting the compound of formula 9a to a compound of formula 10a:

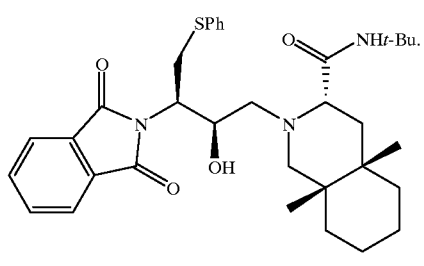
10a
11. A process according to claim 10, further comprising converting the compound of formula 10a to a compound of formula 11a:
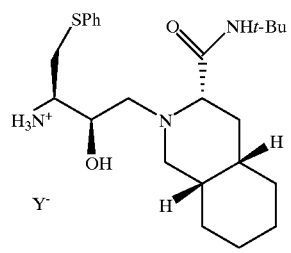
11a
wherein Y⁻ is a suitable salt anion.
12. A process according to claim 11, further comprising converting the compound of formula 11a to a compound of formula 12:
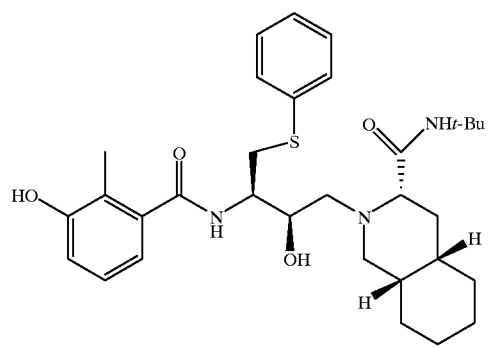
12
and converting the compound of formula 12 to nelfinavir mesylate:
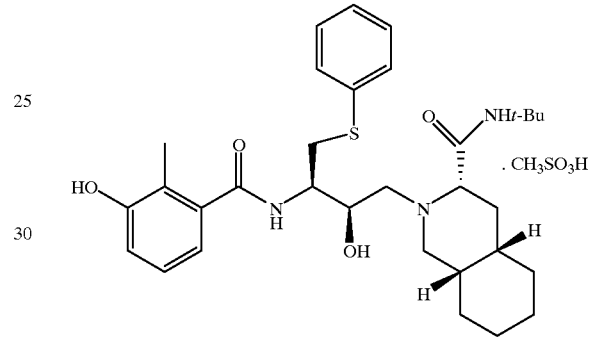
* * * * *

UNITED STATES PATENT AND TRADEMARK OFFICE
CERTIFICATE OF CORRECTION

PATENT NO. : 5,925,759
DATED : July 20, 1999
INVENTOR(S) : Srinivasan Babu et al.

It is certified that error appears in the above-identified patent and that said Letters Patent is hereby corrected as shown below:

Title page,
Item [75], Inventor,
"Travis P. Remarchuk, Irvine;" should read -- Travis P. Remarchuk, Del Mar; --.

Item [56], References Cited, U.S. PATENT DOCUMENTS,

| | | |
|---|---|---|
| "5,705,647 | 1/1998 | Babu et al." should read |
| -- 5,527,829 | 6/1996 | Kalish . . . . . . . . . .514/604 |
| 5,063,208 | 11/1991 | Rosenberg et al . . . . . . 514/19 |
| 5,142,056 | 8/1992 | Kempe et al . . . . . . . . 546/265 |
| 5,157,041 | 10/1992 | Handa et al . . . . . . . . 514/314 |
| 5,196,438 | 3/1993 | Martin et al . . . . . . . 514/311 |
| 5,204,471 | 4/1993 | Negele et al . . . . . . .546/144 |
| 5,235,039 | 8/1993 | Heath, Jr., et al. . . . .530/328 |
| 5,256,783 | 10/1993 | Gokhale et al . . . . . . . 546/146 |
| 5,463,104 | 10/1995 | Vasquez et al . . . . . . . . 564/89 |
| 5,484,926 | 1/1996 | Dressman et al . . . . . .546/114 |
| 5,434,265 | 7/1995 | Fritz et al . . . . . . . . 546/146 |
| 5,514,802 | 5/1996 | Fritz et al . . . . . . . . 546/146 |
| 5,705,647 | 1/1998 | Babu et al . . . . . . . .546/146 --. |

Insert, -- FOREIGN PATENT DOCUMENTS

| | | |
|---|---|---|
| 0490667A2 | 6/1992 | EPO |
| 0402646A1 | 12/1990 | EPO |
| 0337714A2 | 10/1989 | EPO |
| 0432695A2 | 6/1991 | EPO |
| 0432694A2 | 6/1991 | EPO |
| 0526009A1 | 2/1993 | EPO |
| 0533000A1 | 3/1993 | EPO |
| 0346847A2 | 12/1989 | EPO |
| 0539192A1 | 4/1993 | EPO |
| 0361341 A2 | 4/1990 | EPO |
| 0498680A1 | 8/1992 | EPO |
| 94/05639 | 3/1994 | WO |
| 91/08221 | 6/1991 | WO |
| 94/04492 | 3/1994 | WO |
| 93/04043 | 3/1993 | WO |

UNITED STATES PATENT AND TRADEMARK OFFICE
CERTIFICATE OF CORRECTION

PATENT NO.   : 5,925,759  
DATED        : July 20, 1999  
INVENTOR(S)  : Srinivasan Babu et al.

Page 2 of 8

It is certified that error appears in the above-identified patent and that said Letters Patent is hereby corrected as shown below:

| | | |
|---|---|---|
| 93/23379 | 11/1993 | WO |
| 93/13066 | 7/1993 | WO |
| 95/09843 | 4/1995 | WO |
| 97/11938 | 4/1997 | WO |
| 97/11937 | 4/1997 | WO |
| 96/28423 | 9/1996 | WO |
| 97/30993 | 8/1997 | WO |
| 579,223 | 1/1994 | EPO |
| 0560268A1 | 9/1993 | EPO |
| 0434365A2 | 6/1991 | EPO |
| 0356223A2 | 2/1990 | EPO |
| 2,075,666A1 | 2/1993 | Canada --. |

Item [56], References Cited,

Insert, -- OTHER PUBLICATIONS  
Tam et al., J. Med. Chem., 35(7):1318-1320 (1992).

Huff, J. Med. Chem., 34(8):2305-2314 (1991).

Ghosh et al., J. Med. Chem., 36(2):292-294 (1993).

Ghosh et al., J. Med. Chem. 36(16):2300-2310 (1993).

Thompson et al., J. Am. Chem. Soc., 115(2):801-802 (1993).

Rich et al., J. Med. Chem., 34(3):1222-1225 (1991).

Thaisrivongs et al., J. Med. Chem., 34(8):2344-2356 (1991).

Ghosh et al., J. Med. Chem., 36(7):924-927 (1993).

Chong et al., J. Med. Chem., 36:2575-2577 (1993).

Prasad et al., Peptides, Chemistry and Biology, Proceedings of the Twelfth American Peptide Symposium, pp. 721-722 (1991).

UNITED STATES PATENT AND TRADEMARK OFFICE
CERTIFICATE OF CORRECTION

PATENT NO. : 5,925,759
DATED : July 20, 1999
INVENTOR(S) : Srinivasan Babu et al.

It is certified that error appears in the above-identified patent and that said Letters Patent is hereby corrected as shown below:

Rich et al., Chem. Abstracts, 114(15) Abstract No. 143998g (1991).

Houpis et al., Tetrahedron Letters, 34(16):2593-2596 (1993).

Roberts, et al., Science, 248:358-361 (1990).

Gilbert et al., J. Chem. Soc. Perkin Trans., 2:475-479 (1993).

Young et al., J. Med. Chem., 35(10):1702-1709 (1992).

Lyle et al., J. Med. Chem., 34(3):1228-1230 (1991).

Peltier et al., "Contribution à l'ètude du groupe carboxylique. Absorption infrarouge et ionisation," Bulletin de la Socièté chimique de France, 1960, 1141-1147.

Mukharji et al., Indian J. Chem., EN, 9, 1971, 515-523, as abstracted in DATABASE XFIRE< Beilstein, 3-methoxy-2-methyl-benzoic acid ethyl ester.

Ratner et al., Complete nucleotide sequence of the AIDS virus, HTLV-111", NATURE, Vol. 313, January 24, 1985

Rose et al., "Regulation of Autoproteolysis of the HIV-1 and HIV-2 Proteases with Engineered Amino Acid Substitutions", Journal of Biological Chemistry, Vol. 268, No. 16, pp. 11939-11945 (1993)

Menge et al., "Structure-Function Analysis of the Mammalian DNA Polymerase Active Site: role of Aspartic Acid 256, Arginine 254, and Arginine 258 in Nucleotidyl Transfer", Biochemistry 1995, 34, 19934-15942

Celis et al., "Chain-terminating Mutants Affecting a Periplasmic Binding Protein Involved in the Active Transport of Arginine and Ornithine in Escherichia coli", Journal of Biological Chemistry, Vol. 256, No. 2, pp. 773 779, 1981

UNITED STATES PATENT AND TRADEMARK OFFICE
CERTIFICATE OF CORRECTION

PATENT NO. : 5,925,759
DATED : July 20, 1999
INVENTOR(S) : Srinivasan Babu et al.

It is certified that error appears in the above-identified patent and that said Letters Patent is hereby corrected as shown below:

Morrison, Kinetics of the reversible Inhibition of Enzyme-Catalysed Reactions by Tight-Binding Inhibitors", Biochim. Biophys. Acta, 185 (1969) 269-286

Alley, et al., "Feasibility of Drug Screening with Panels of Human Tumor Cell Lines Using a Microculture Tetrazolium Assay", Cancer Research, 48, 589-601, February 1, 1988

J. Townsend, et al., "Novel Copper Complexes of Chiral Diphosphines: Preparation, Structure, and Use to Form Rhodium Complex Catalysts for Chiral Hydrogenations", J. Org. Chem., 1980, 45, pp. 2995-2999.

Mash et al., "1,4-Di-o-alkyl Threitols from Tartaric Acid", Org. Synthesis, Coll. Vol. VIII, pp. 155-161.

S. Takano, et al., "Selective Manipulation of Hydroxy Groups in (2S, 3S)-Threitol", Synthesis, October 1986, pp.811-817.

T. Ozturk, et al., "Synthesis of a Chiral Monosubstituted Derivative of Bis (ethylenedithio)tetrathiafulvalene: Reaction of the Cyclic Sulfate Ester of R,R-1,4 Difluorobutane-2,3-diol with 2-Thioxo-1,3-dithiole-4,5-dithiolate", J. Mater. Chem., 1995, 5(10), 1553-1556.

K. Vanhessche et al., "Catalytic Asymmetric Synthesis of New Halogenated Chiral Synthons", Chem. Eur. J. 1997, 3. No. 4.

Gao et al., "Vicinal Diol Cyclic Sulfates: Like Epoxides Only More Reactive", J. Am. Chem. Soc. 1988, 110, 7538-7539

UNITED STATES PATENT AND TRADEMARK OFFICE
CERTIFICATE OF CORRECTION

PATENT NO. : 5,925,759
DATED : July 20, 1999
INVENTOR(S) : Srinivasan Babu et al.

It is certified that error appears in the above-identified patent and that said Letters Patent is hereby corrected as shown below:

Column 3,
Lines 5-10,

" 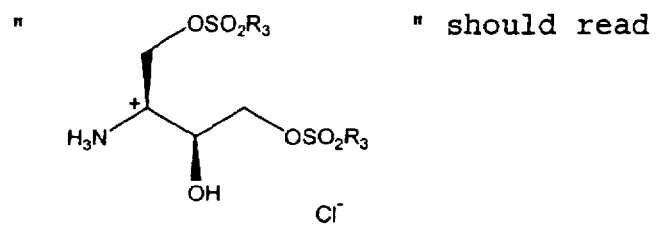 " should read

-- 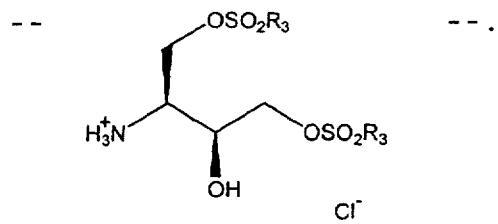 --.

Column 5,
Lines 55-63,

" 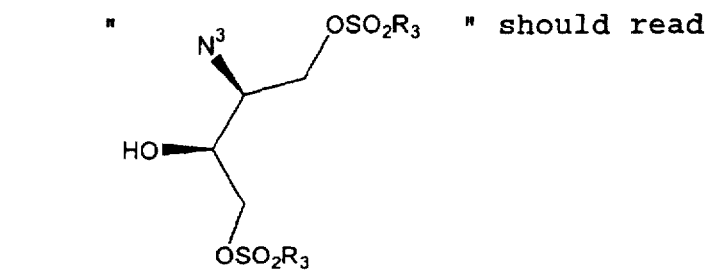 " should read

-- 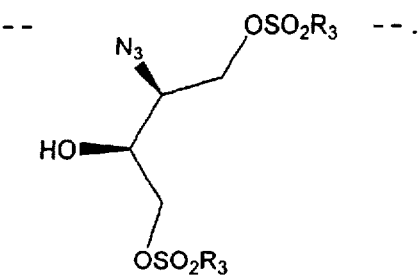 --.

UNITED STATES PATENT AND TRADEMARK OFFICE
CERTIFICATE OF CORRECTION

PATENT NO. : 5,925,759
DATED : July 20, 1999
INVENTOR(S) : Srinivasan Babu et al.

It is certified that error appears in the above-identified patent and that said Letters Patent is hereby corrected as shown below:

Column 12,
Line 34, "$C_1$-$C_5$" should read -- $C_1$-$C_6$ --.

Column 15,
Line 40, "methoxyenzoates" should read -- methoxybenzoates --.

Column 17,
Line 37, "keta), should read -- ketal, --.

Column 19,
Line 20, "FtOAc" should read -- EtOAc --;
Line 33, "NaIo$_4$" should read -- NaIO$_4$ --;
Lines 47-56, " 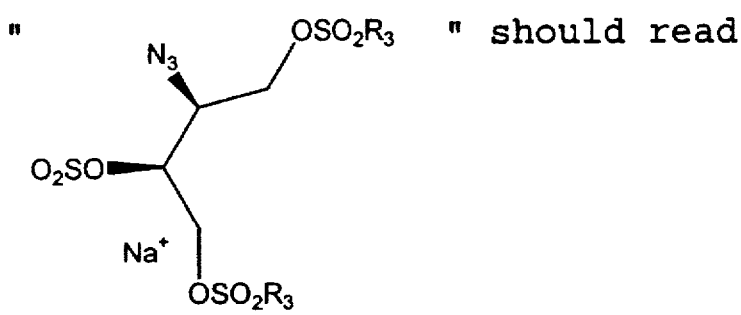 " should read -- 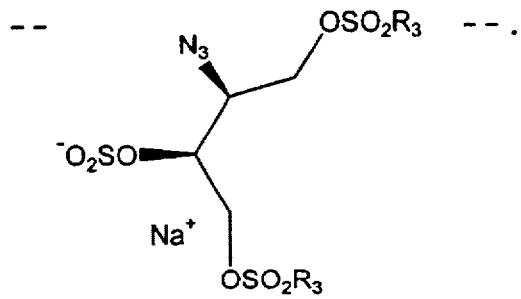 --.

UNITED STATES PATENT AND TRADEMARK OFFICE
CERTIFICATE OF CORRECTION

PATENT NO. : 5,925,759
DATED : July 20, 1999
INVENTOR(S) : Srinivasan Babu et al.

It is certified that error appears in the above-identified patent and that said Letters Patent is hereby corrected as shown below:

Column 23,
Scheme 3, first line of Scheme:

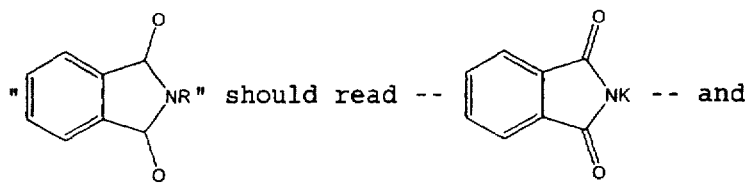

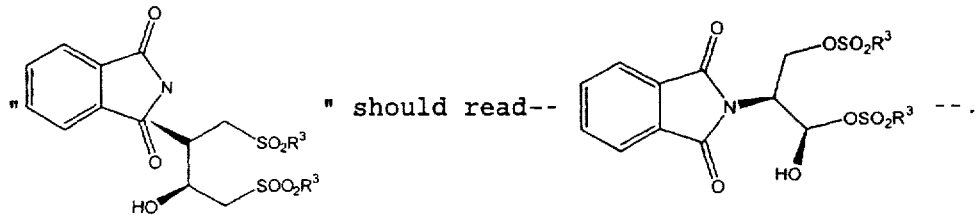

Column 24,
Line 5, "usefull" should read -- useful --.

Column 32,
Line 55, "which" should read -- which was --.

UNITED STATES PATENT AND TRADEMARK OFFICE
CERTIFICATE OF CORRECTION

PATENT NO. : 5,925,759
DATED : July 20, 1999
INVENTOR(S) : Srinivasan Babu et al.

It is certified that error appears in the above-identified patent and that said Letters Patent is hereby corrected as shown below:

Column 33,
Line 15,

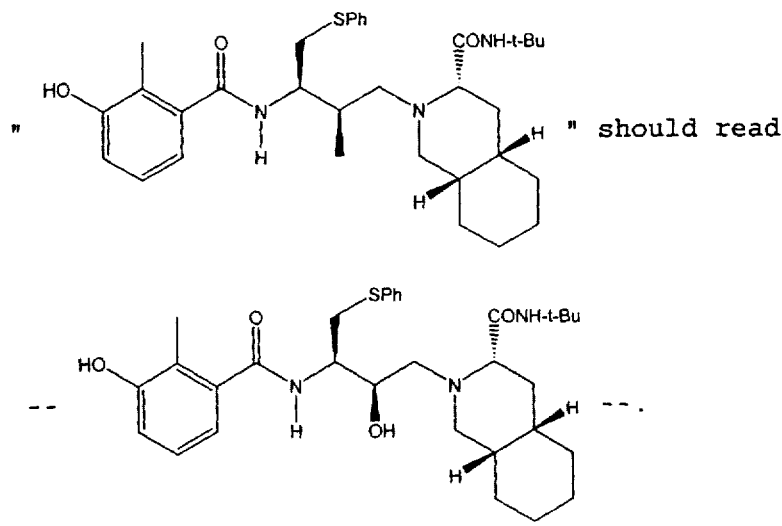

Column 34,
Line 24, "stir" should read -- to stir --.

Column 37,
Line 28, "2.5% Hcl" should read -- 2.5% HCl --.

Signed and Sealed this

Twelfth Day of March, 2002

Attest:

JAMES E. ROGAN
*Attesting Officer*   *Director of the United States Patent and Trademark Office*